(12) United States Patent
Kandula

(10) Patent No.: US 11,312,707 B2
(45) Date of Patent: Apr. 26, 2022

(54) COMPOSITIONS AND METHODS FOR THE TREATMENT OF FUNGAL INFECTIONS

(71) Applicant: CELLIX BIO PRIVATE LIMITED, Hyderabad (IN)

(72) Inventor: Mahesh Kandula, Andhra Pradesh (IN)

(73) Assignee: Cellix Bio Private Limited, Hyderabad (IN)

( * ) Notice: Subject to any disclaimer, the term of this patent is extended or adjusted under 35 U.S.C. 154(b) by 58 days.

(21) Appl. No.: 16/464,377

(22) PCT Filed: Nov. 24, 2017

(86) PCT No.: PCT/IB2017/057388
§ 371 (c)(1),
(2) Date: May 28, 2019

(87) PCT Pub. No.: WO2018/096497
PCT Pub. Date: May 31, 2018

(65) Prior Publication Data
US 2020/0361912 A1    Nov. 19, 2020

(30) Foreign Application Priority Data

Nov. 28, 2016 (IN) .............................. 201641040639
Apr. 7, 2017 (IN) .............................. 201741012687

(51) Int. Cl.
| | |
|---|---|
| *A61P 1/02* | (2006.01) |
| *C07C 211/03* | (2006.01) |
| *C07C 211/21* | (2006.01) |
| *C07D 233/64* | (2006.01) |
| *C07D 405/14* | (2006.01) |
| *C07D 233/60* | (2006.01) |
| *C07D 233/62* | (2006.01) |
| *C07D 239/22* | (2006.01) |
| *C07D 403/06* | (2006.01) |

(52) U.S. Cl.
CPC .............. *C07D 405/14* (2013.01); *A61P 1/02* (2018.01); *C07C 211/03* (2013.01); *C07C 211/21* (2013.01); *C07D 233/60* (2013.01); *C07D 233/62* (2013.01); *C07D 233/64* (2013.01); *C07D 239/22* (2013.01); *C07D 403/06* (2013.01)

(58) Field of Classification Search
CPC ................................................... C07D 233/64
See application file for complete search history.

(56) References Cited

U.S. PATENT DOCUMENTS

2005/0070551 A1    3/2005 Remenar et al.
2009/0082363 A1    3/2009 Czarnik et al.

FOREIGN PATENT DOCUMENTS

WO    2015/095346 A1    6/2015

OTHER PUBLICATIONS

Tarsa. European Journal of Pharmaceutical Sciences, 2010, 41, 23-30 (Year: 2010).*
Mittapalli. Crystal Growth and Design, 2015, 15, 2493-2504 (Year: 2015).*
Buechel. STN recordof Drugs Made in Germany, 1972, 15(3), 79-80,82, 84-90, 92-4, available online May 12, 1984. (Year: 1972).*
Tarsa. STN record of European Journal of Pharmaceutical Sciences, 2010, 41, 23-30, available on STN Jul. 21, 2010 (Year: 2010).*
Pohl et al., "Antifugal free fatty acids: A Review", *Science Against Microbial Pathogens: Communicating Current Research and Technological Advances*. Jan. 1, 2011, pp. 61-71.
International Search Report issued in PCT/IB2017/057388 dated May 16, 2018 (6 pages).
C. Garcia-Cuesta et al., "Current Treatment of Oral Candidiasis: A Literature Review", Journal of Clinical and Experimental Dentistry, dated Jan. 1, 2014 (7 pages).
J. Vazquez, "Optimal Management of Oropharyngeal and Esophageal Candidiasis in Patients Living With HIV Infection", HIV/AIDS-Research and Palliative Care, dated Apr. 27, 2010 (13 pages).
G.K.E.Scriba, "Phenytoin-Lipid Conjugates: Chemical, Plasma Esterase-Mediated, and Pancreatic Lipase-Mediated Hydrolysis In Vitro", Pharmaceutical Research, vol. 10, No. 8, Jan. 11, 1993 (2 pages).
(English translation of "Phenytoin-Lipid Conjugates as Potential Prodrugs of Phenytoin Phenytoin-Lipid-Konjugate ALS Potentielle Prodrugs DES Phenytoins", Archiv Der Pharmazie, dated Jan. 1, 1993.).

* cited by examiner

*Primary Examiner* — Noble E Jarrell
(74) *Attorney, Agent, or Firm* — S. Elizabeth Miller, Esq.

(57) ABSTRACT

The invention relates to the compounds or its pharmaceutical acceptable polymorphs, solvates, enantiomers, stereoisomers and hydrates thereof. The pharmaceutical compositions comprising an effective amount of compounds of formula I, formula II, formula III, formula IV, formula V, formula VI, formula VII, formula VIII, formula IX or Formula X and, the methods for the treatment of fungal infections may be formulated for oral, buccal, rectal, topical, transdermal, transmucosal, lozenge, spray, intravenous, oral solution, buccal mucosal layer tablet, parenteral administration, syrup, or injection. Such compositions may be used to treatment of fungal infections.

8 Claims, 11 Drawing Sheets

(E)-4-((1,3-bis(dodecanoyloxy)propan-2-yl)oxy)-4-oxobut-2-enoate 4-(4-(((3R,5R)-5-((1H-1,2,4-triazol-1-yl)methyl)-5-(2,4-difluorophenyl)tetrahydrofuran-3-yl) methoxy)phenyl)-1-(4-(1-((2S,3S)-2-hydroxypentan-3-yl)-5-oxo-1,5-dihydro-4H-1,2,4-triazol-4-yl)phenyl)piperazin-1-ium (10): CLX-SYN-G159-C09E

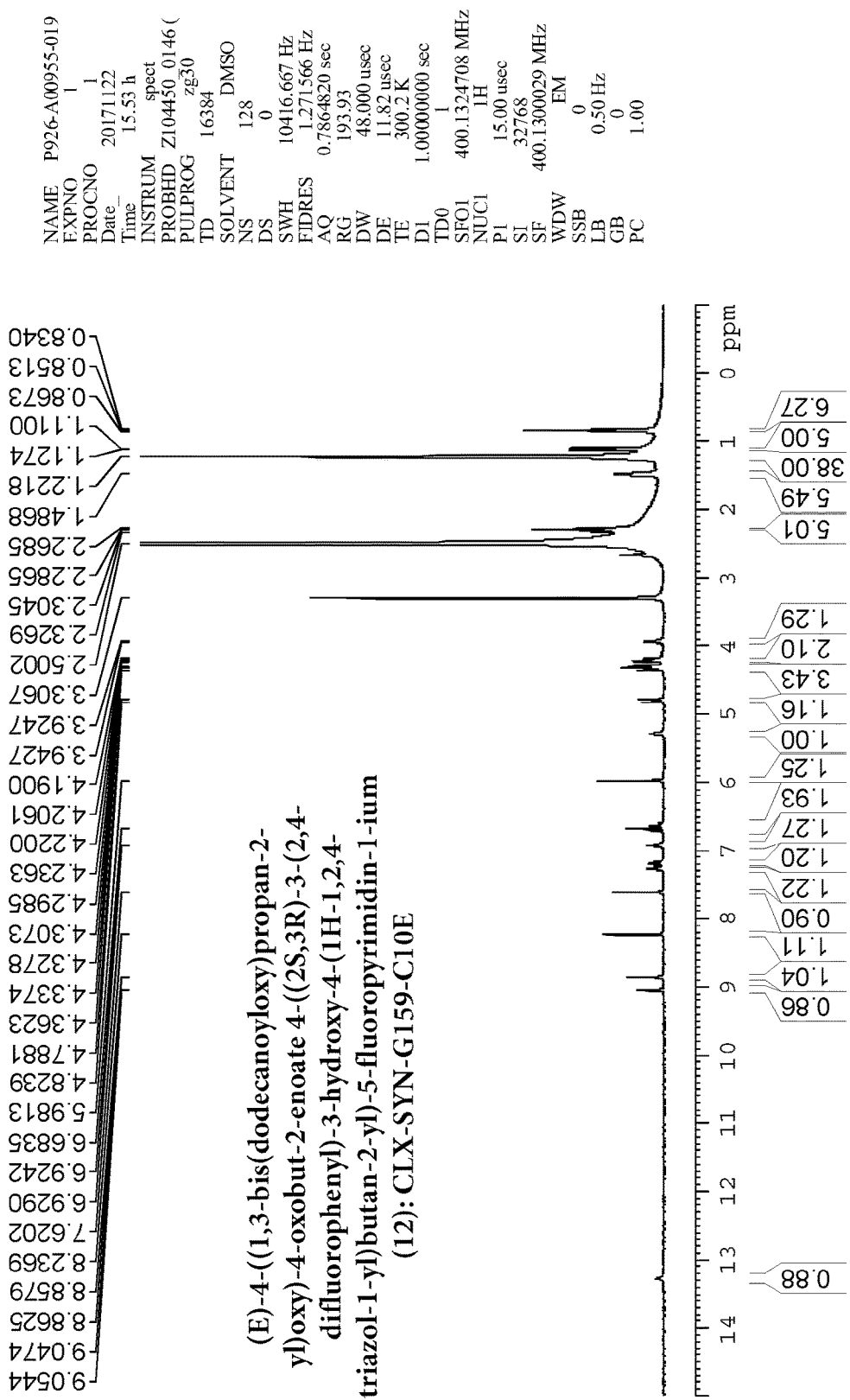

COMPOSITIONS AND METHODS FOR THE TREATMENT OF FUNGAL INFECTIONS

PRIORITY

The present application is a U.S. National Phase of International Patent Application No. PCT/IB2017/057388, filed Nov. 24, 2017, which claims the benefit of Indian Provisional Patent Application No. 201641040639 filed on Nov. 28, 2016, and Indian Provisional Patent Application No. 201741012687 filed on Apr. 7, 2017, the entire disclosures of which are relied on for all purposes and are incorporated into this application by reference.

FIELD OF THE INVENTION

This disclosure generally relates to compounds and compositions for the treatment of fungal infections. More particularly, this invention relates to treating subjects with a pharmaceutically acceptable dose of compounds, crystals, solvates, enantiomer, stereoisomer, esters, hydrates, or mixtures thereof.

BACKGROUND OF THE INVENTION

Invasive infection due to *Candida* species is largely a condition associated with medical progress, and is widely recognized as a major cause of morbidity and mortality in the healthcare environment. There are at least 15 distinct *Candida* species that cause human disease, but >90% of invasive disease is caused by the 5 most common pathogens, *C. albicans, C. glabrata, C. tropicalis, C. parapsilosis*, and *C. krusei*. Each of these organisms has unique virulence potential, antifungal susceptibility, and epidemiology, but taken as a whole, significant infections due to these organisms are generally referred to as invasive candidiasis.

Oropharyngeal candidiasis is the current term used to describe disease of the linings of the oral cavity caused almost always by *Candida albicans*. Disease caused by *Candida* species, including oropharyngeal candidiasis, encompasses a broad spectrum, from the trivial to the most life-threatening of infections. Because the fungus is believed to reside in low numbers on mucous membranes in the healthy host, disease is attributable to a reduction in host defenses, and the host response depends in great measure on where lesions arise. For example, in the most common presentation of oropharyngeal candidiasis, pseudomembranous candidiasis, Gram staining of the curd-like lesions on buccal membranes demonstrates a tangle of oral bacteria, proliferating fungus (predominately blastoconidia and pseudohyphae), and polymorphonuclear leukocytes in an eosinophilic background.

Other forms of oropharyngeal candidiasis manifest as glossitis or erythema in the fissures of the mouth or beneath denture plates. Furthermore, changes in environmental factors can prompt the development of adaptive responses in individual microorganisms to new environmental conditions and introduce more pathogenic microorganisms into the microbial community. Non-mutans streptococci and *Actinomyces* are predominant in the supragingival ecosystem that cause acidification, resulting in both demineralization of tooth surface and introduction of more cariogenic microorganisms, mutans streptococci, to the ecosystem.

*Fusobacteria* and *Prevotella* neutralize subgingival environment pH by nitrogenous metabolism and stimulate GCF efflux. The neutral pH and nitrogenous environment increases the proteolytic activity of *Prevotella* and facilitates the establishment of a more acid-intolerant, but periodontopathogenic bacterium, *Porphyromonas gingivalis*.

Managing acute pathology of often relies on the addressing underlying pathology and symptoms of the disease. There is currently a need in the art for new compositions to treatment or delay of the onset of fungal infections and its associated complications progression.

SUMMARY OF THE INVENTION

The present invention provides compounds, compositions containing these compounds and methods for using the same to treat, prevent and/or ameliorate the effects of the conditions such as fungal infections.

The invention herein provides compositions comprising of formula I or pharmaceutical acceptable hydrates or solvates thereof. The invention also provides pharmaceutical compositions comprising one or more compounds of formula I or intermediates thereof and one or more of pharmaceutically acceptable carriers, vehicles or diluents. These compositions may be used in the treatment of fungal infections and its associated complications.

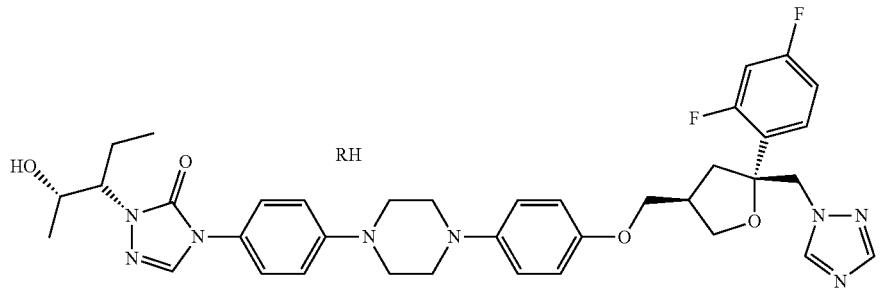

Formula I and pharmaceutically acceptable hydrates, solvates, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid, arachidonic acid or

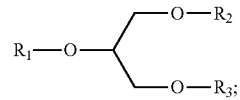

wherein, within the proviso
each $R_1$, $R_2$ and $R_3$ independently represents

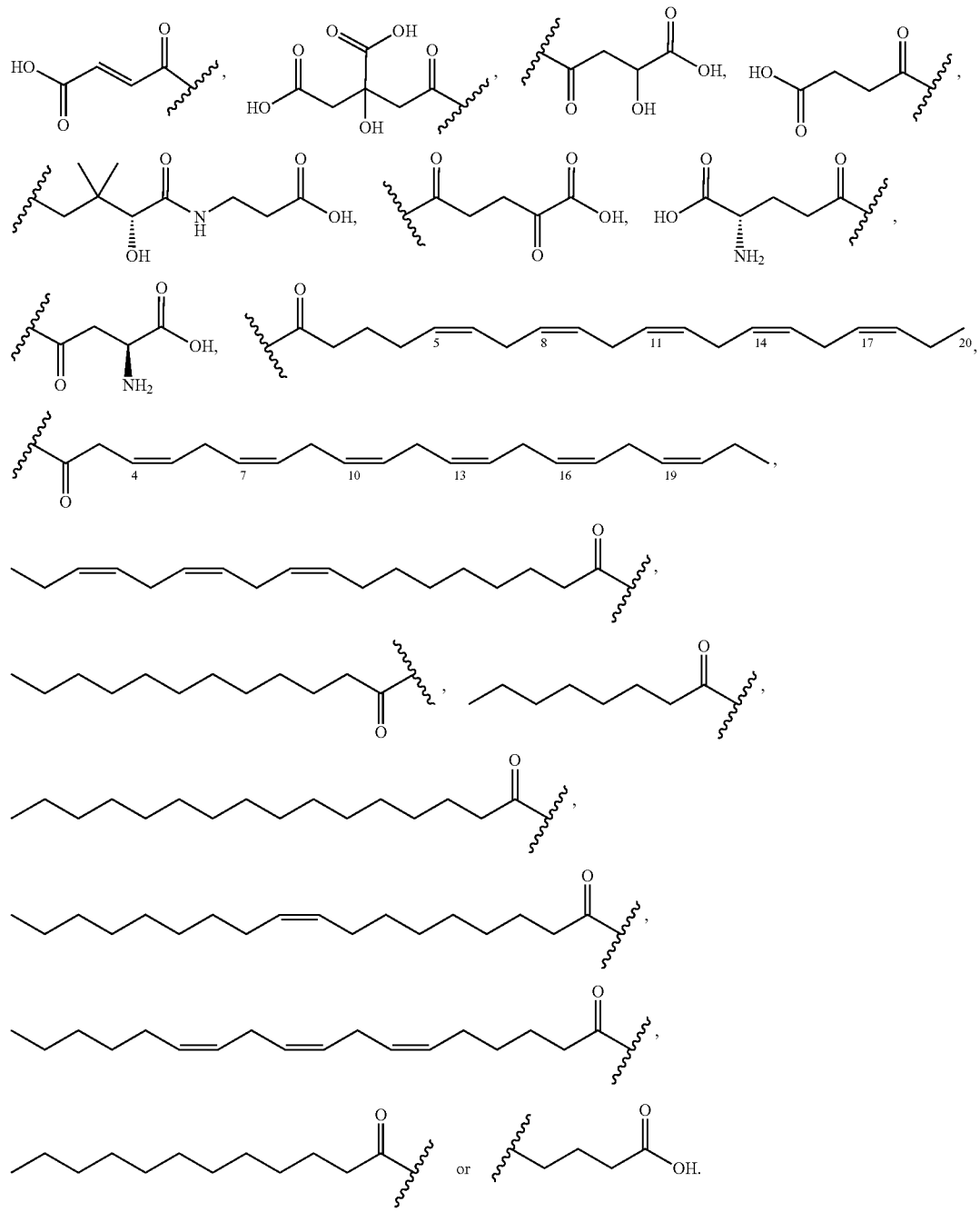

In another aspect, the compounds of formula II are described:

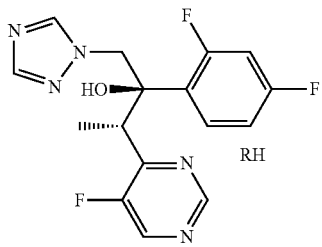

Formula II and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid and arachidonic acid or

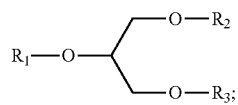

wherein,
each $R_1$, $R_2$ and $R_3$ independently represents

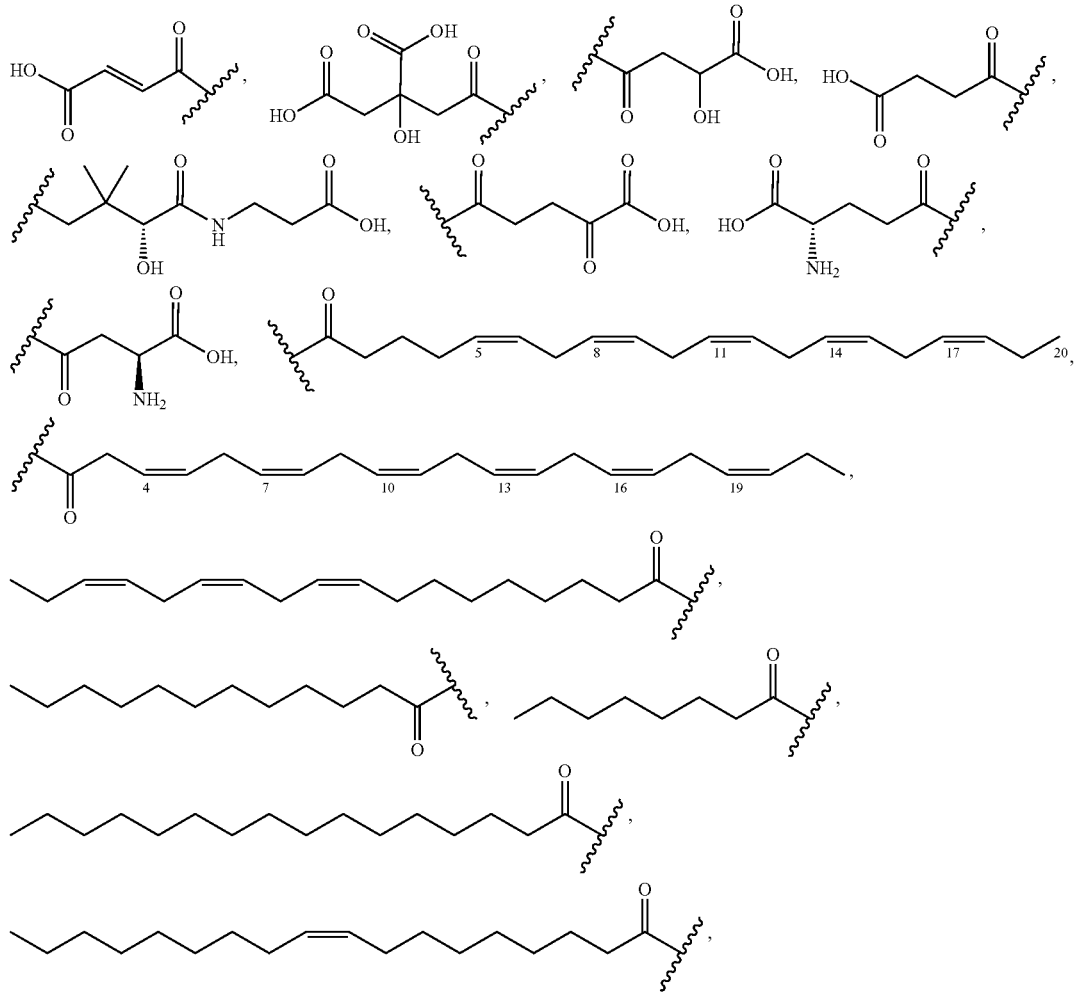

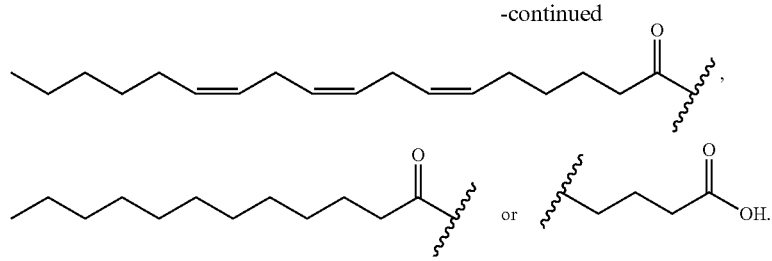

In certain embodiments, the compounds of formula III are described:

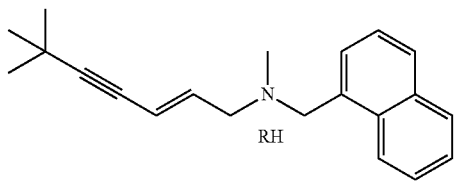

Formula III and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid and arachidonic acid or

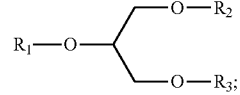

wherein,
each $R_1$, $R_2$ and $R_3$ independently represents

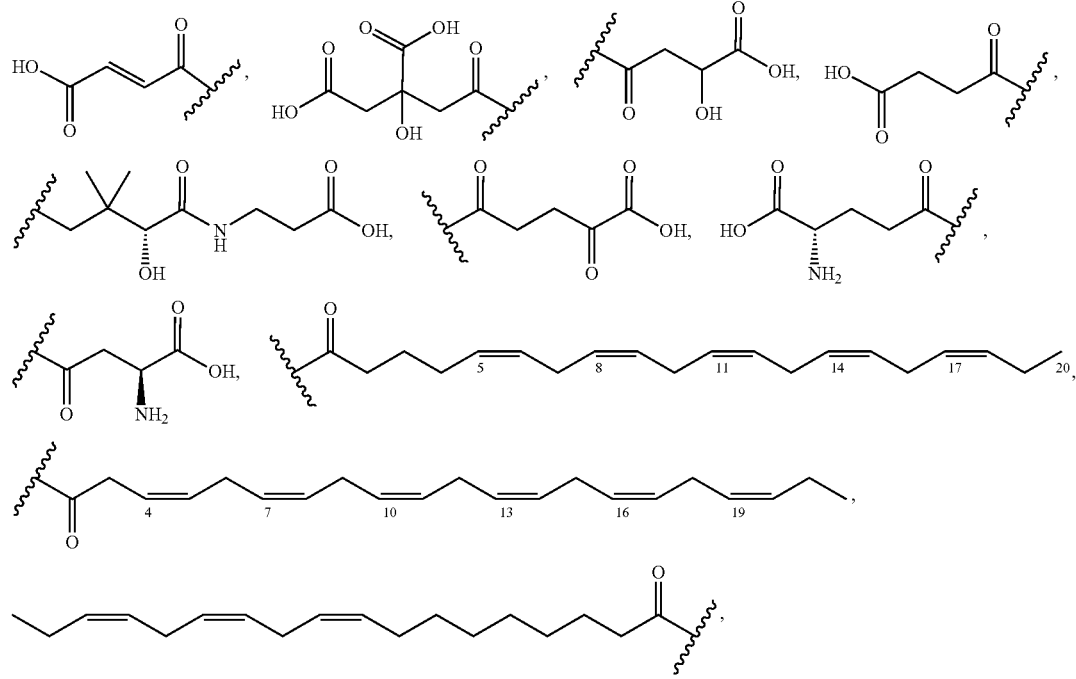

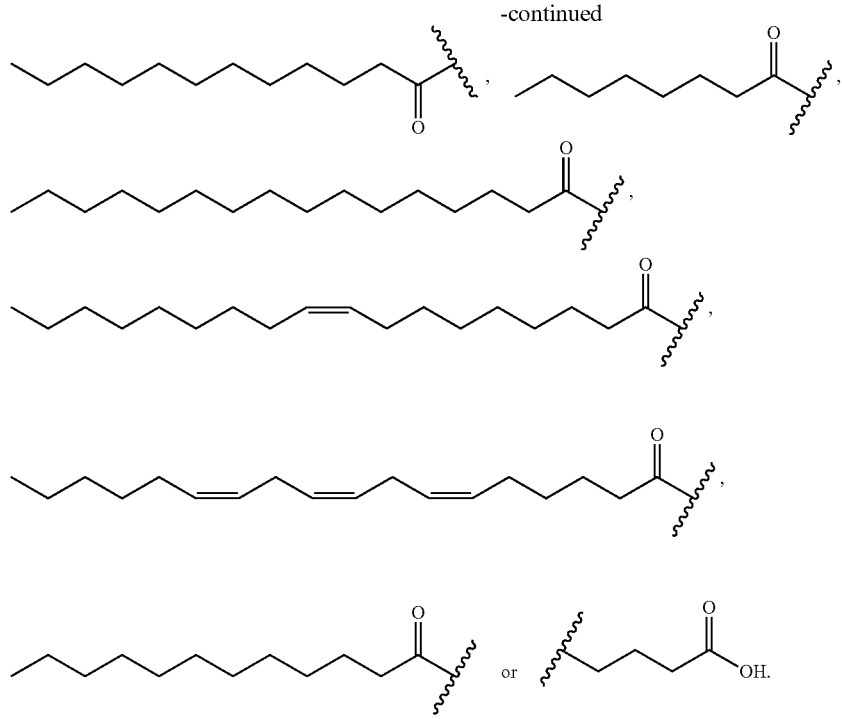

In an additional aspect, the compounds of formula IV are described:

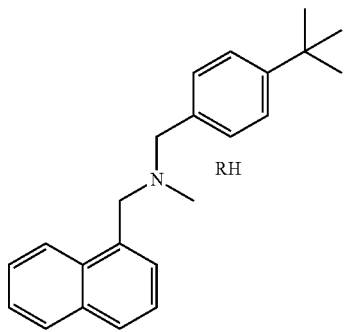

Formula IV and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid, arachidonic acid or

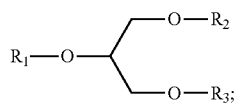

wherein,
each $R_1$, $R_2$ and $R_3$ independently represents

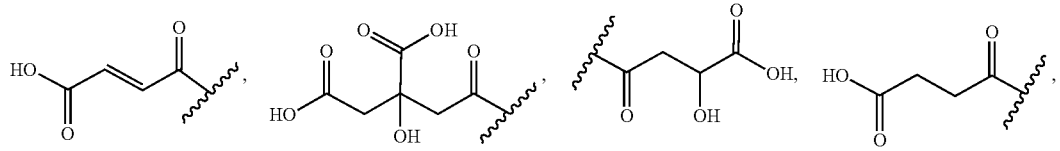

-continued

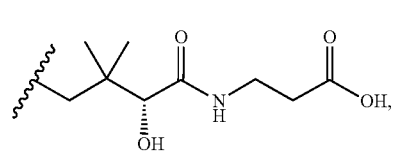 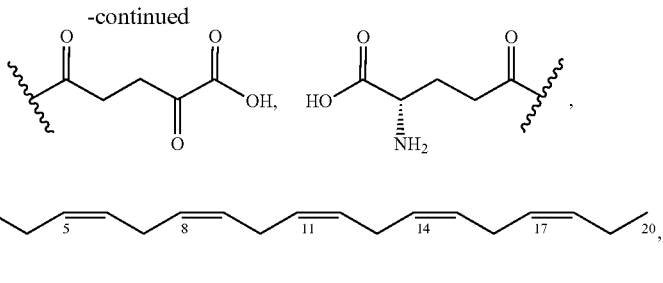

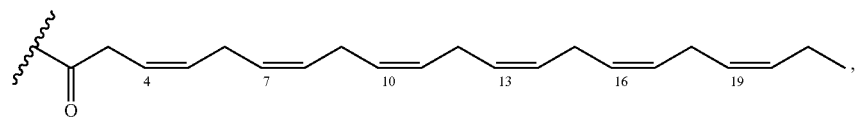

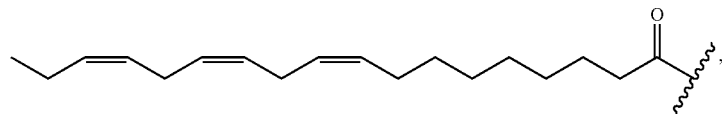

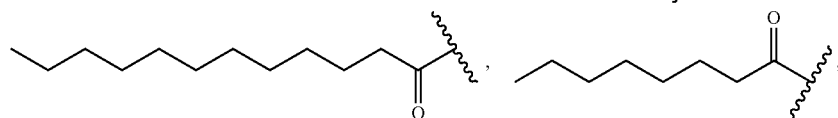

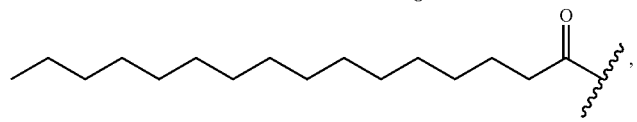

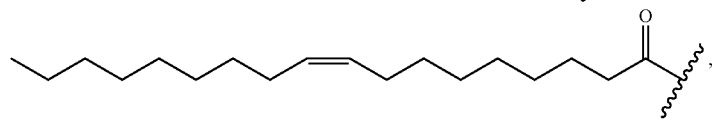

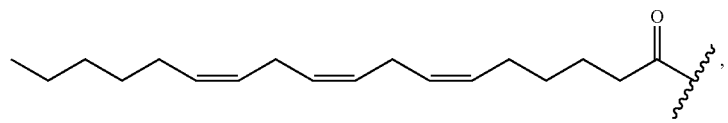

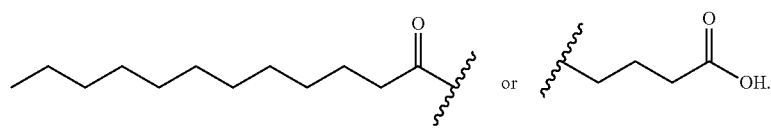 [SMILES: *C(=O)CCCCCCCCCCC ; *CCCC(=O)O]

In an additional aspect, the compounds of formula V are described:

Formula V

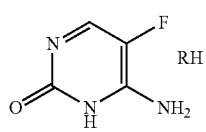

and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid and arachidonic acid or

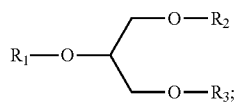

wherein, each $R_1$, $R_2$ and $R_3$ independently represents

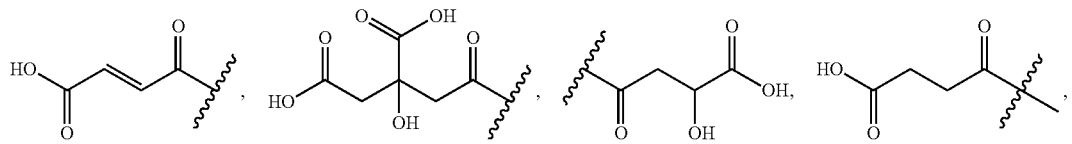

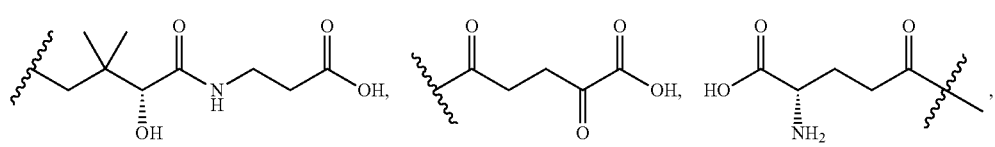

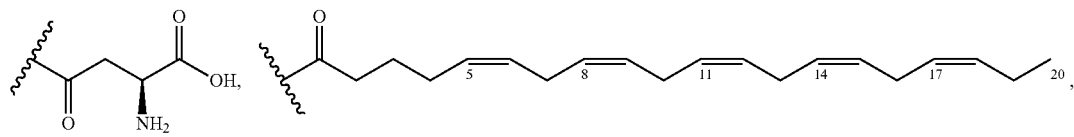

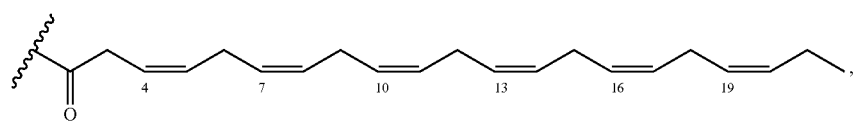

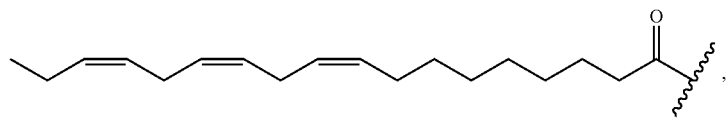

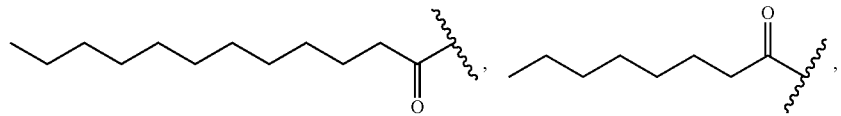

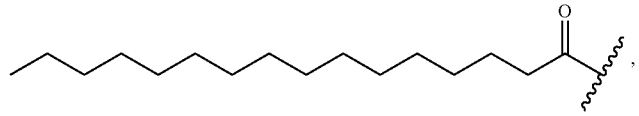

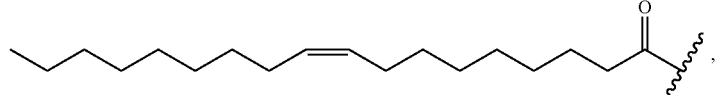

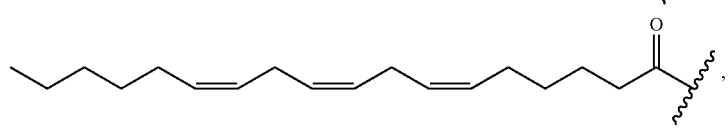

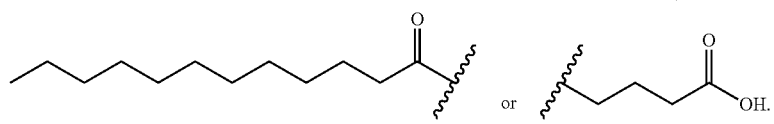

In an additional aspect, the compounds of formula VI are described:

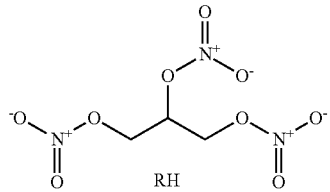

Formula VI and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid and arachidonic acid or

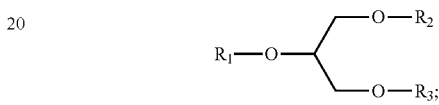

wherein, each $R_1$, $R_2$ and $R_3$ independently represents

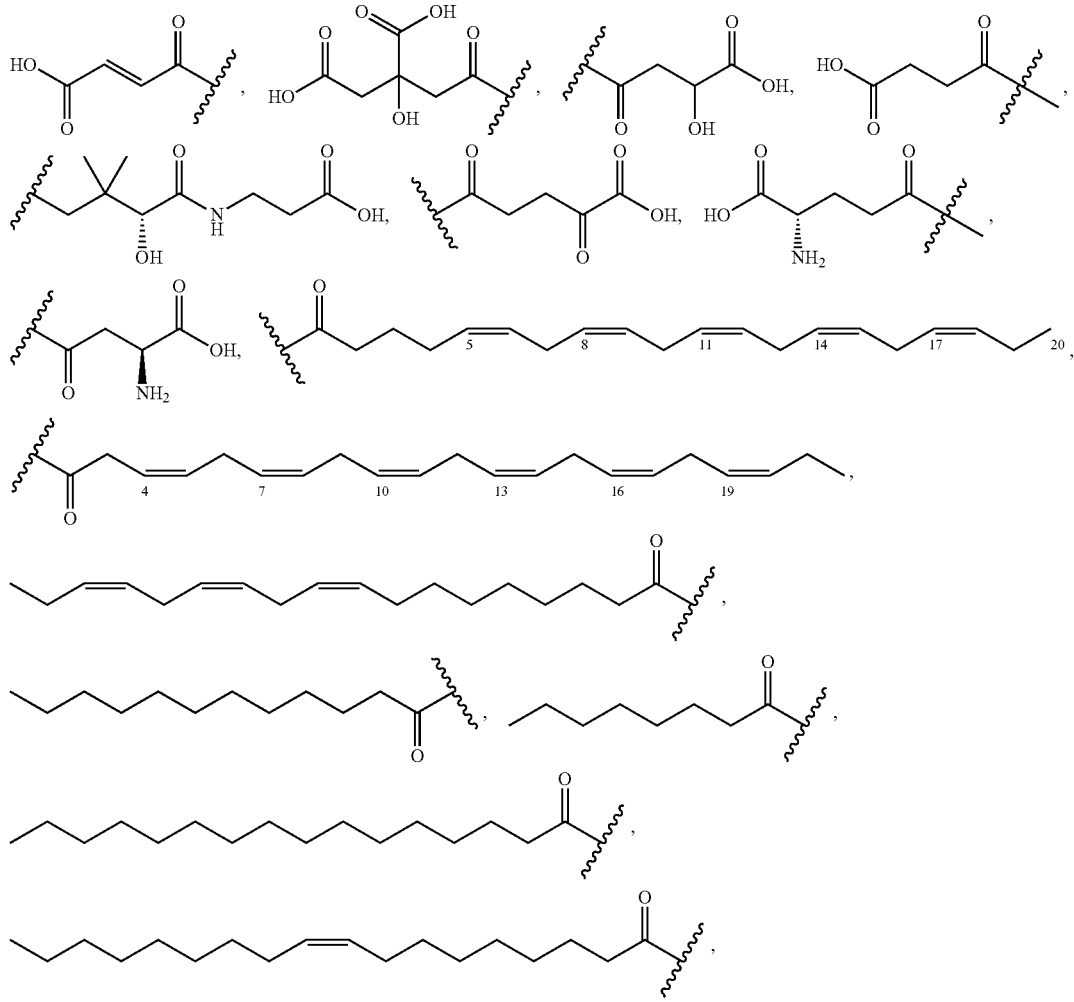

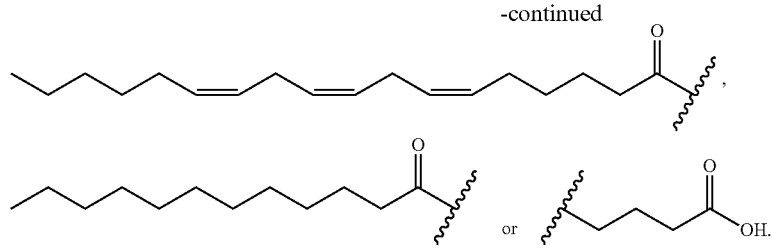
In an additional aspect, the compounds of formula VII are described:
Formula VII
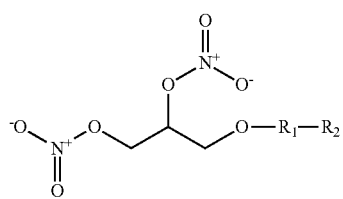
$R_1$ is selected from OD, OCH$_3$, OCOCH$_3$, NULL,
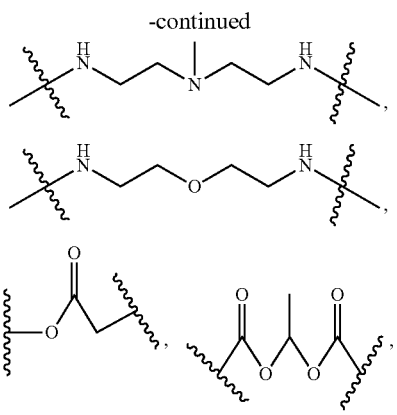
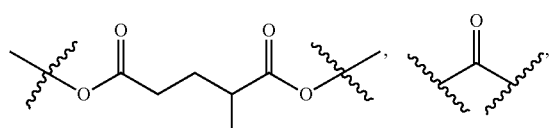
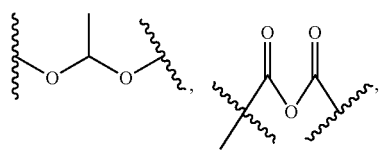
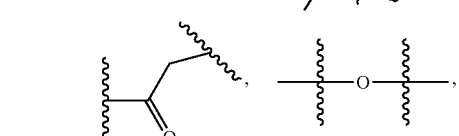
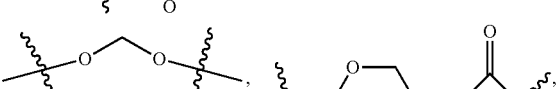
$R_2$ is
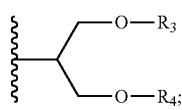
wherein,
each $R_3$ and $R_4$ independently represents
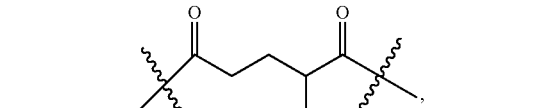
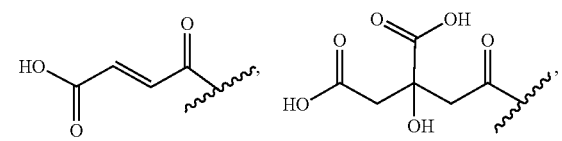

-continued

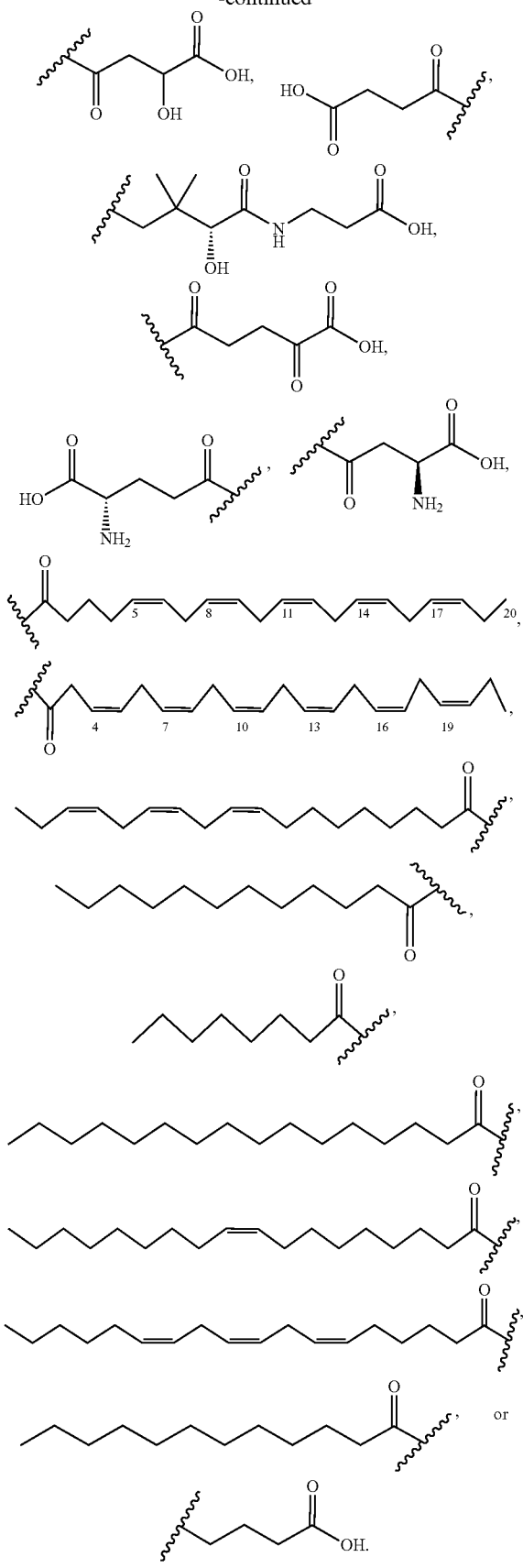

In another aspect, the compounds of formula VIII are described:

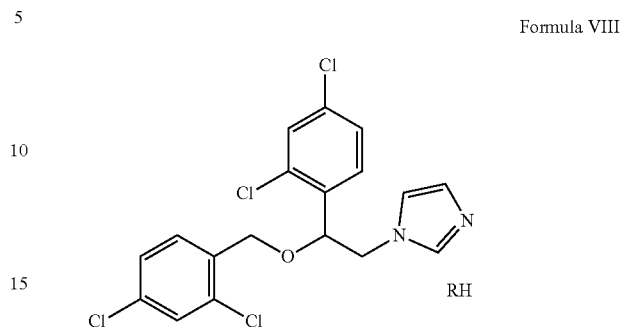

Formula VIII and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid and arachidonic acid or

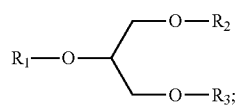

wherein,
each $R_1$, $R_2$ and $R_3$ independently represents

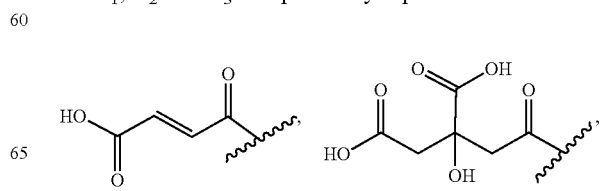

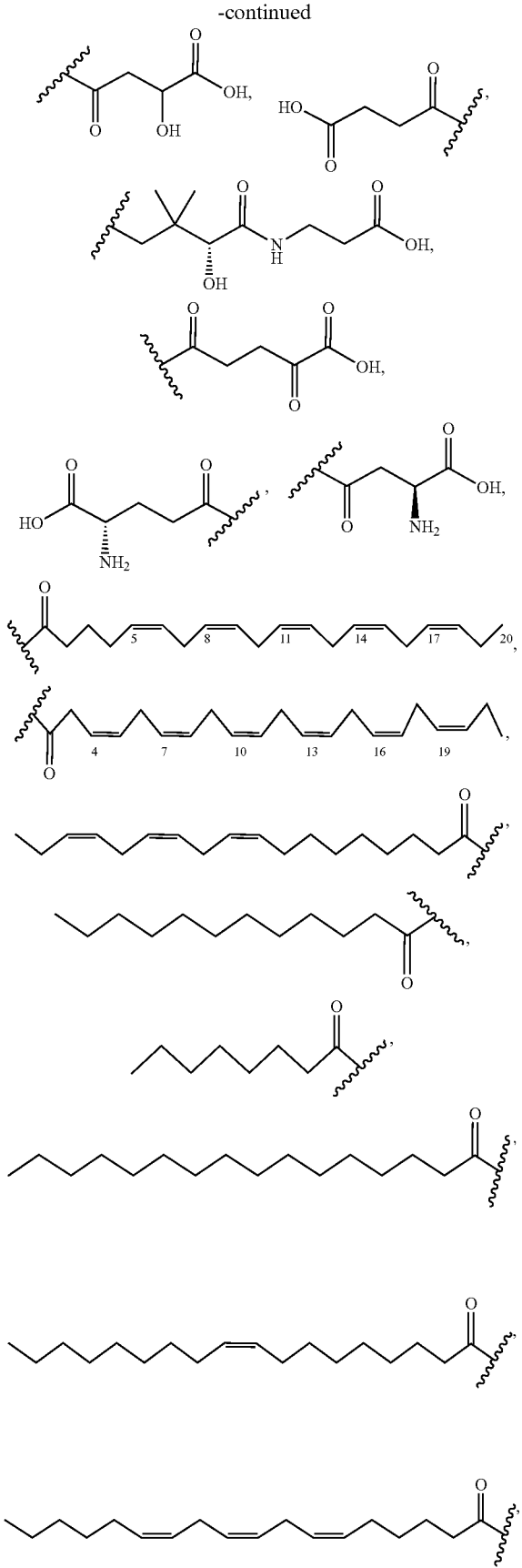

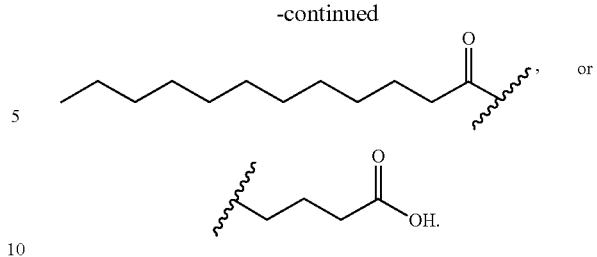

In another aspect, the compounds of formula IX are described:

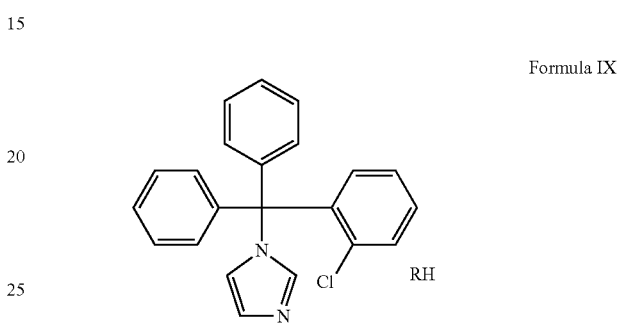

Formula IX and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid and arachidonic acid or

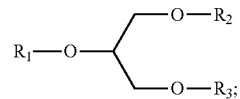

wherein,
each $R_1$, $R_2$ and $R_3$ independently represents
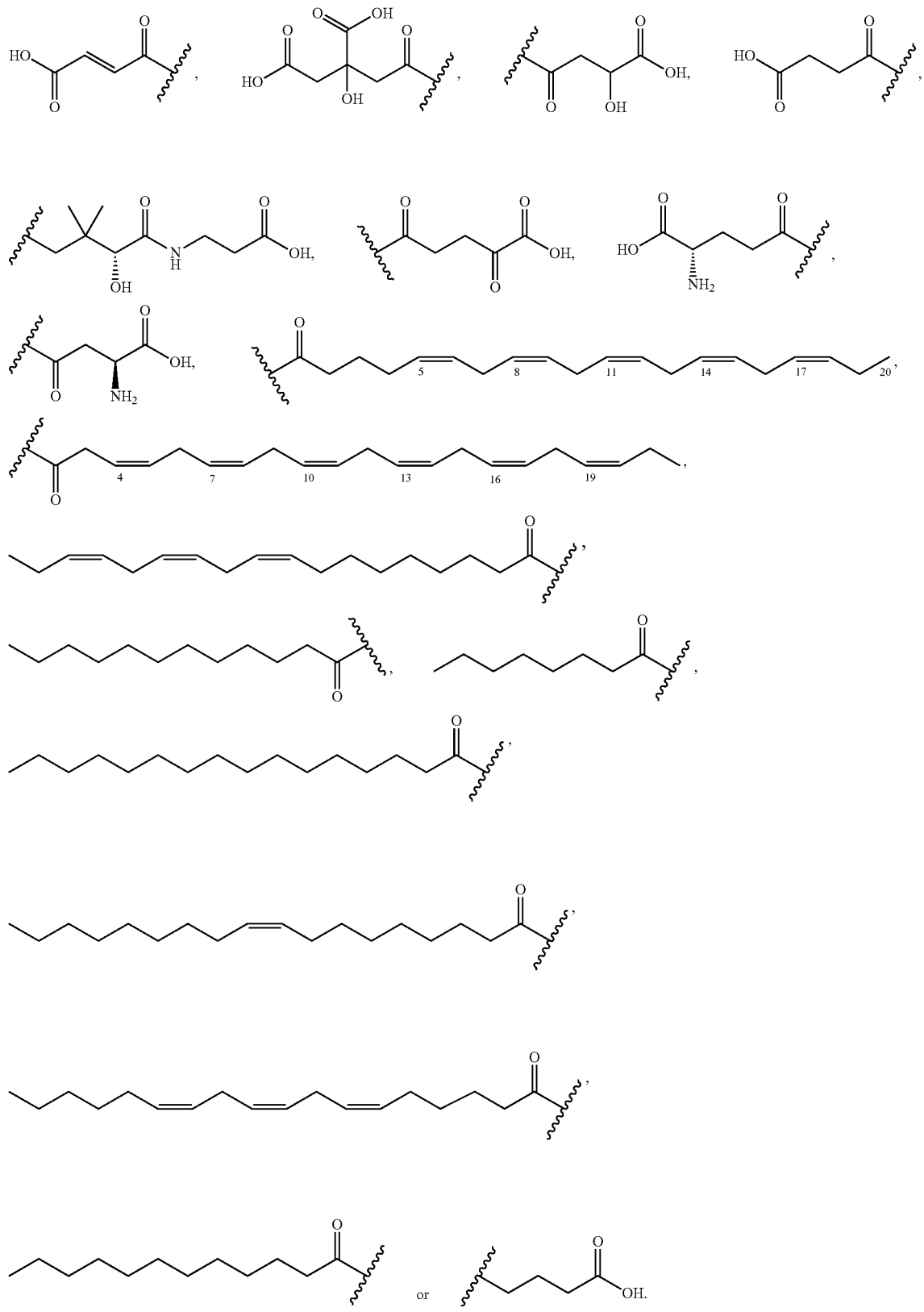

In another aspect, the compounds of formula X are described:

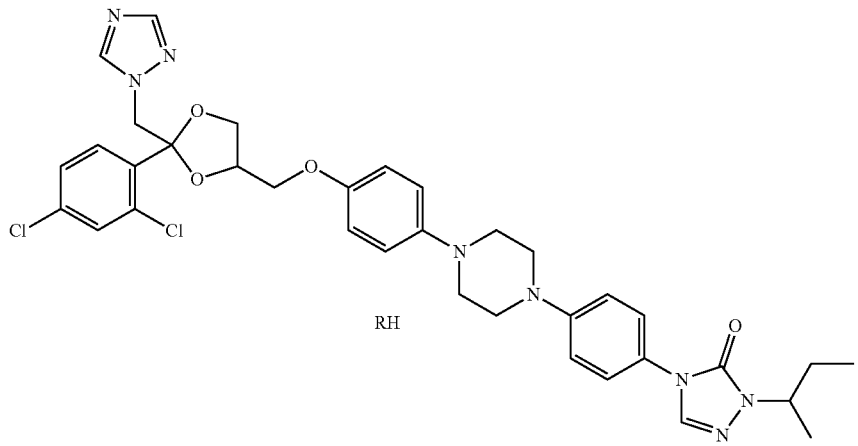

Formula X and pharmaceutically acceptable hydrates, solvates, prodrugs, enantiomers, and stereoisomers thereof;

wherein, RH is selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, stearic acid, oleic acid, elaidic acid, linoleic acid, linolenic acid, linolelaidic acid and arachidonic acid or

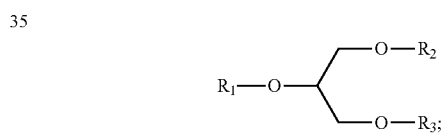

wherein, each $R_1$, $R_2$ and $R_3$ independently represents

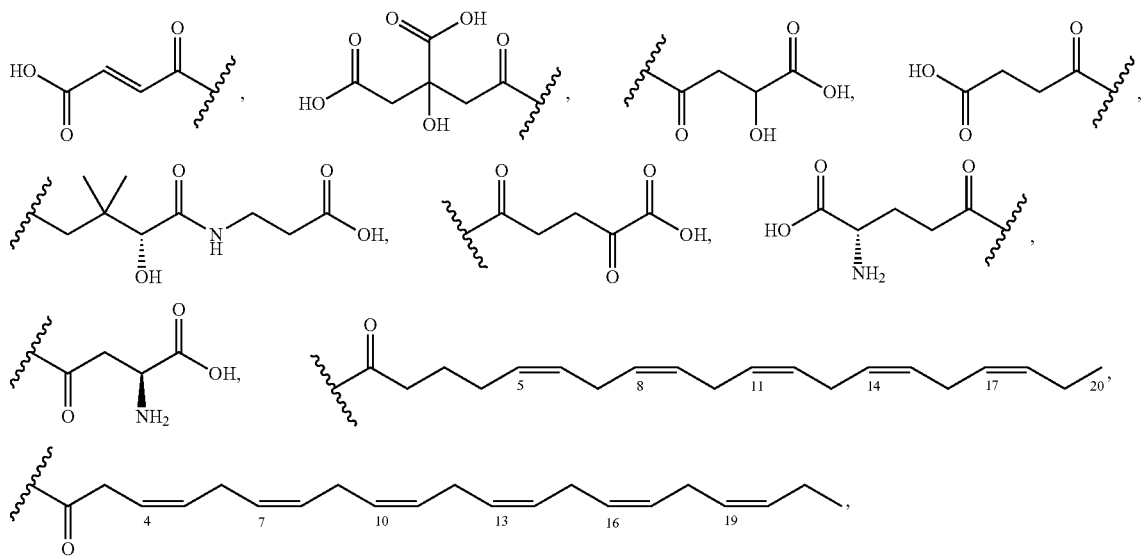

-continued

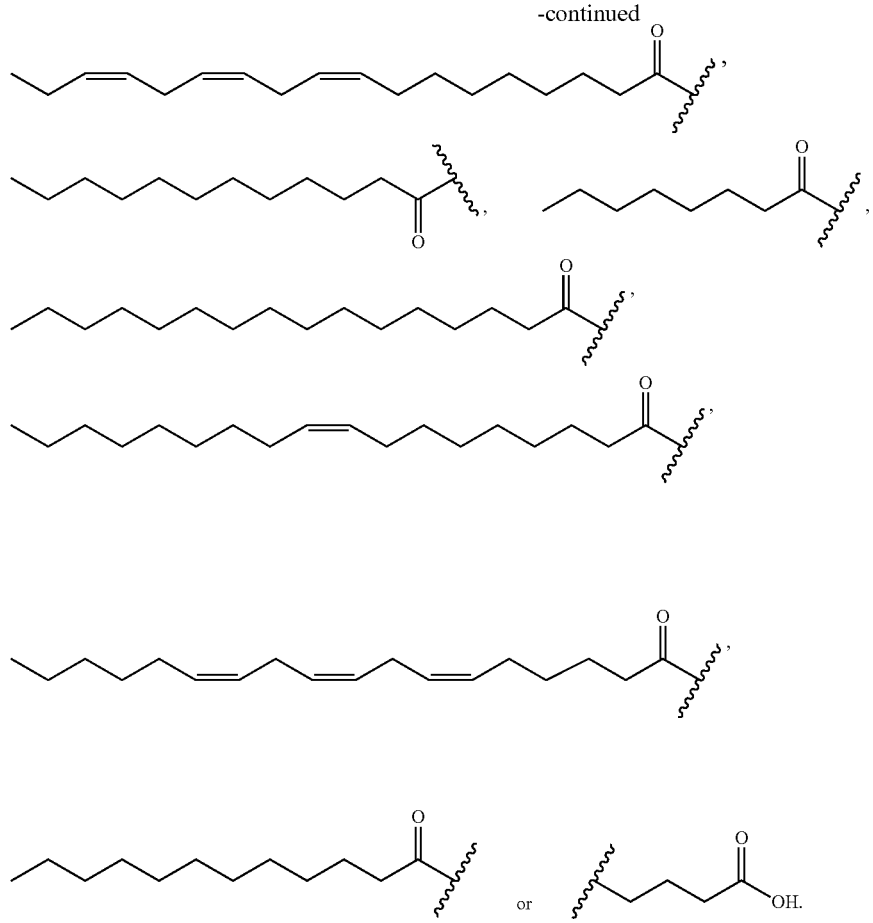

Herein the application also provides a kit comprising any of the pharmaceutical compositions disclosed herein. The kit may comprise instructions for use in the treatment of fungal infections or its related complications.

The application also discloses a pharmaceutical composition comprising a pharmaceutically acceptable carrier and any of the compositions herein. In some aspects, the pharmaceutical composition is formulated for oral solution, oral rinsing solution, oral antiseptic solution, systemic administration, oral administration, sustained release, parenteral administration, injection, subdermal administration, or transdermal administration.

Herein, the application additionally provides kits comprising the pharmaceutical compositions described herein.

The kits may further comprise instructions for use in the treatment of fungal infections or its related complications.

The compositions described herein have several uses. The present application provides, for example, methods of treating a patient suffering from fungal infections or its related complications manifested from metabolic or genetic conditions or disorders, metabolic diseases, chronic diseases or disorders; neurodegenerative disorders, metabolic condition, Hepatology, Cancer, Respiratory, Hematological, Orthopedic, Cardiovascular, Renal, Skin, Vascular or Ocular complications.

In the illustrative embodiments, examples of compounds of formula I, formula II, formula III, formula IV, formula V, formula VI, formula VII, formula VIII, formula IX and Formula X are as set forth below:

Formula I

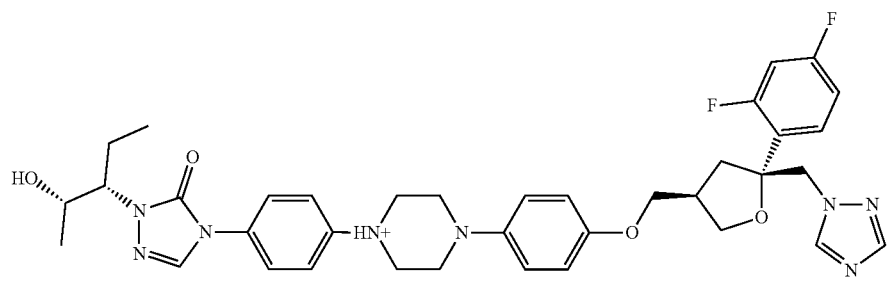

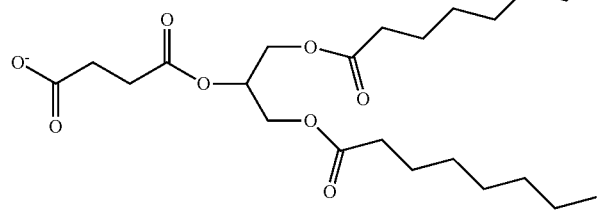
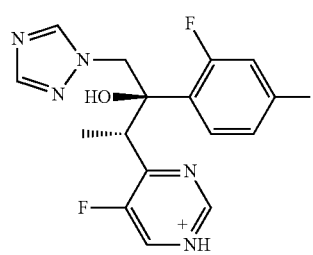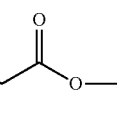
Formula II
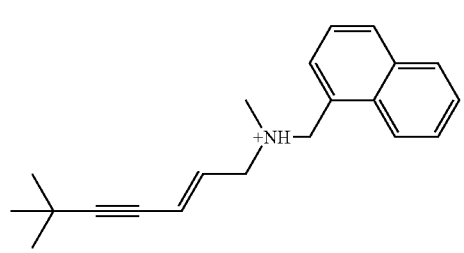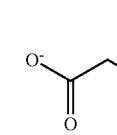
Formula III
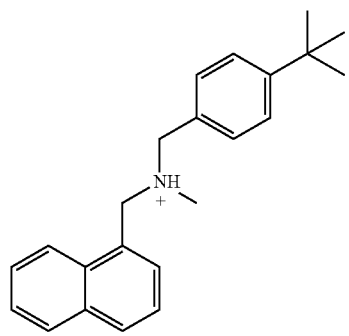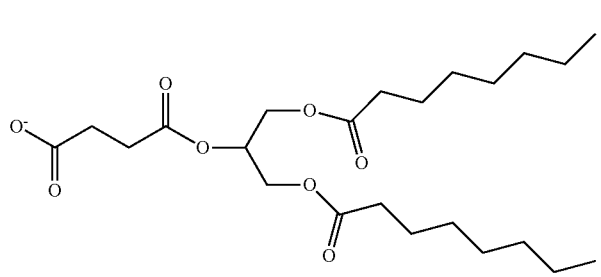
Formula IV
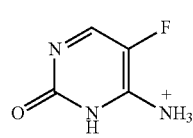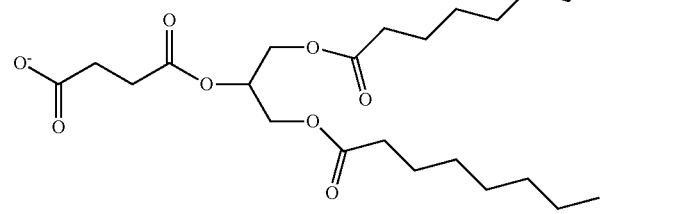
Formula V
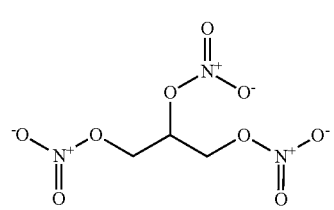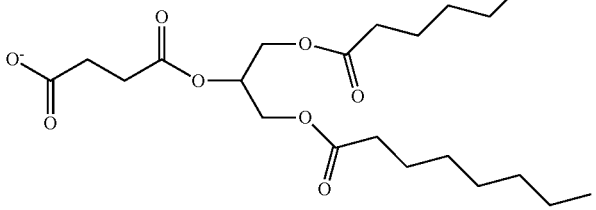
Formula VI -continued
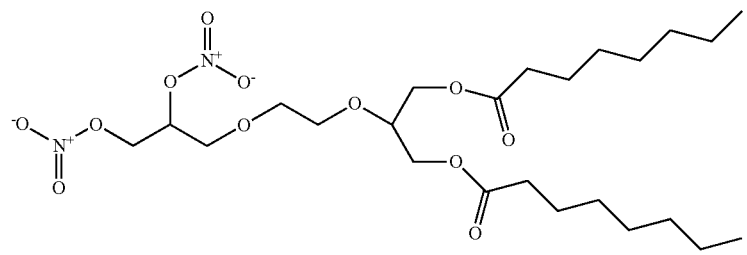
Formula VII
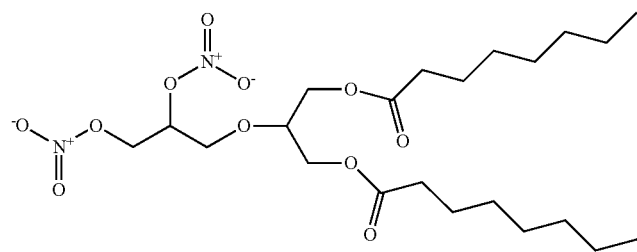
Formula VII
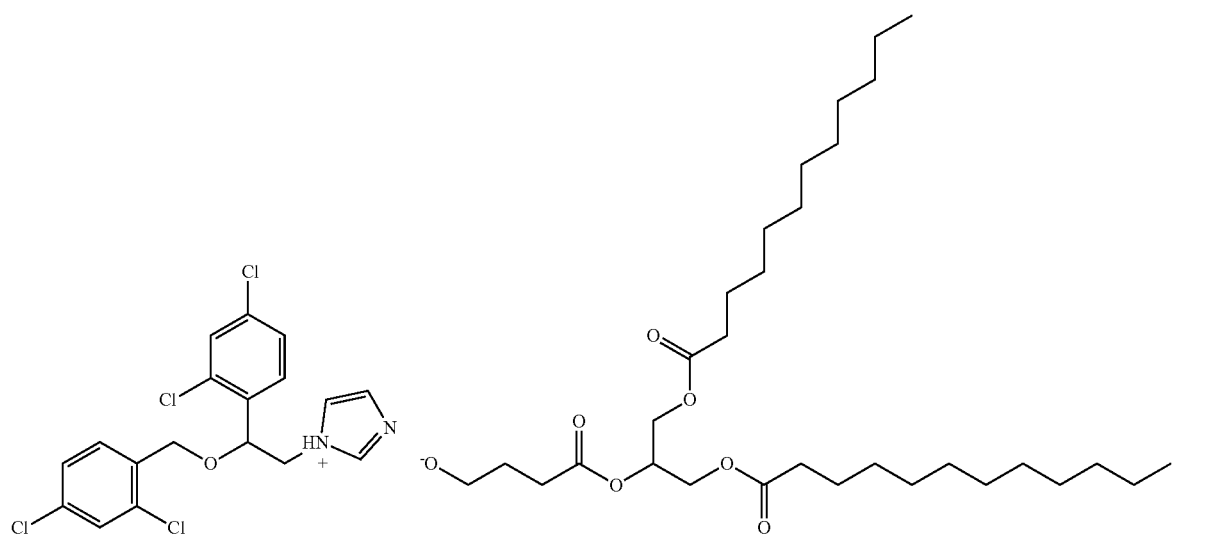
Formula VIII
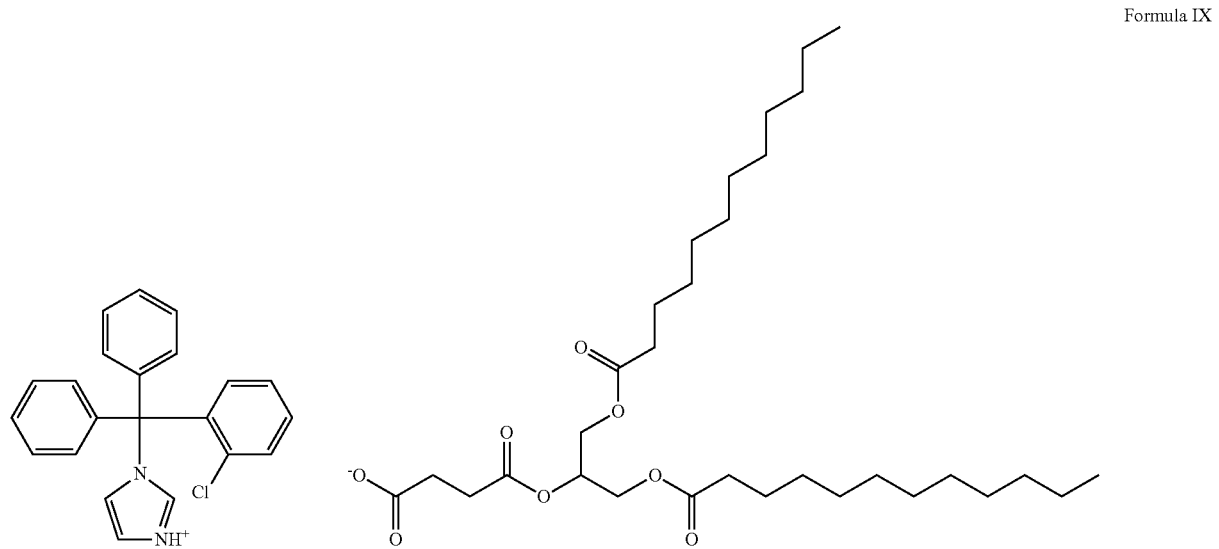
Formula IX -continued
Formula X
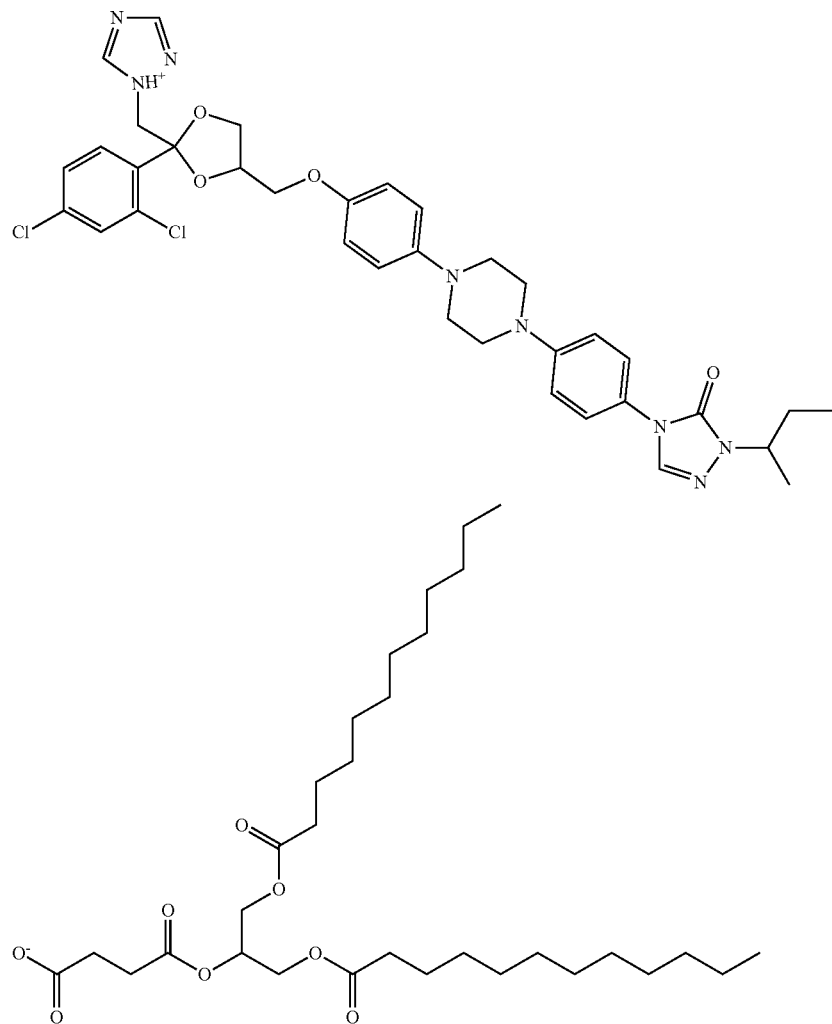
Formula X
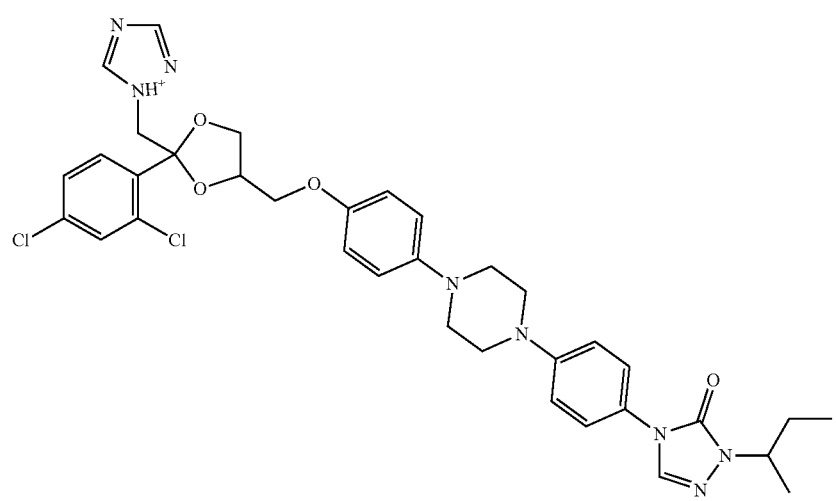

-continued

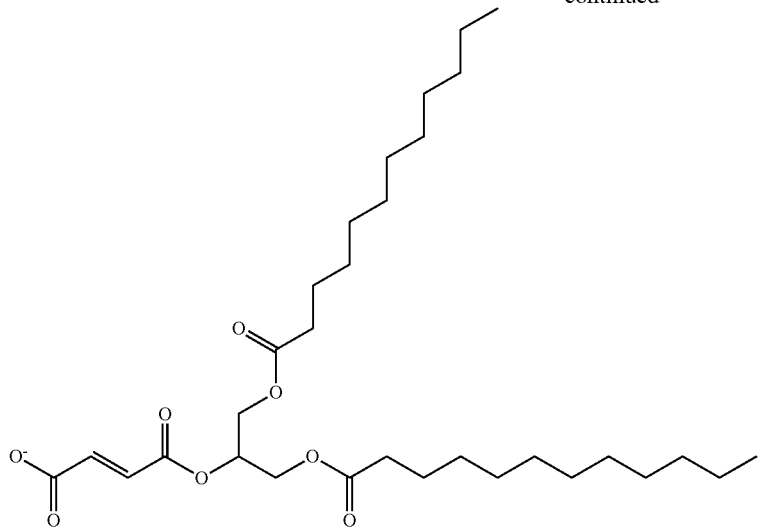

BRIEF DESCRIPTION OF THE FIGURES

FIG. 11 shows an NMR spectra of compound (E)-4-((1,3-bis(dodecanoyloxy)propan-2-yl)oxy)-4-oxobut-2-enoate 4-((2S,3R)-3-(2,4-difluorophenyl)-3-hydroxy-4-(1H-1,2,4-triazol-1-yl)butan-2-yl)-5-fluoropyrimidin-1-ium (12).

DETAILED DESCRIPTION OF THE INVENTION

Definitions

Figure 1:
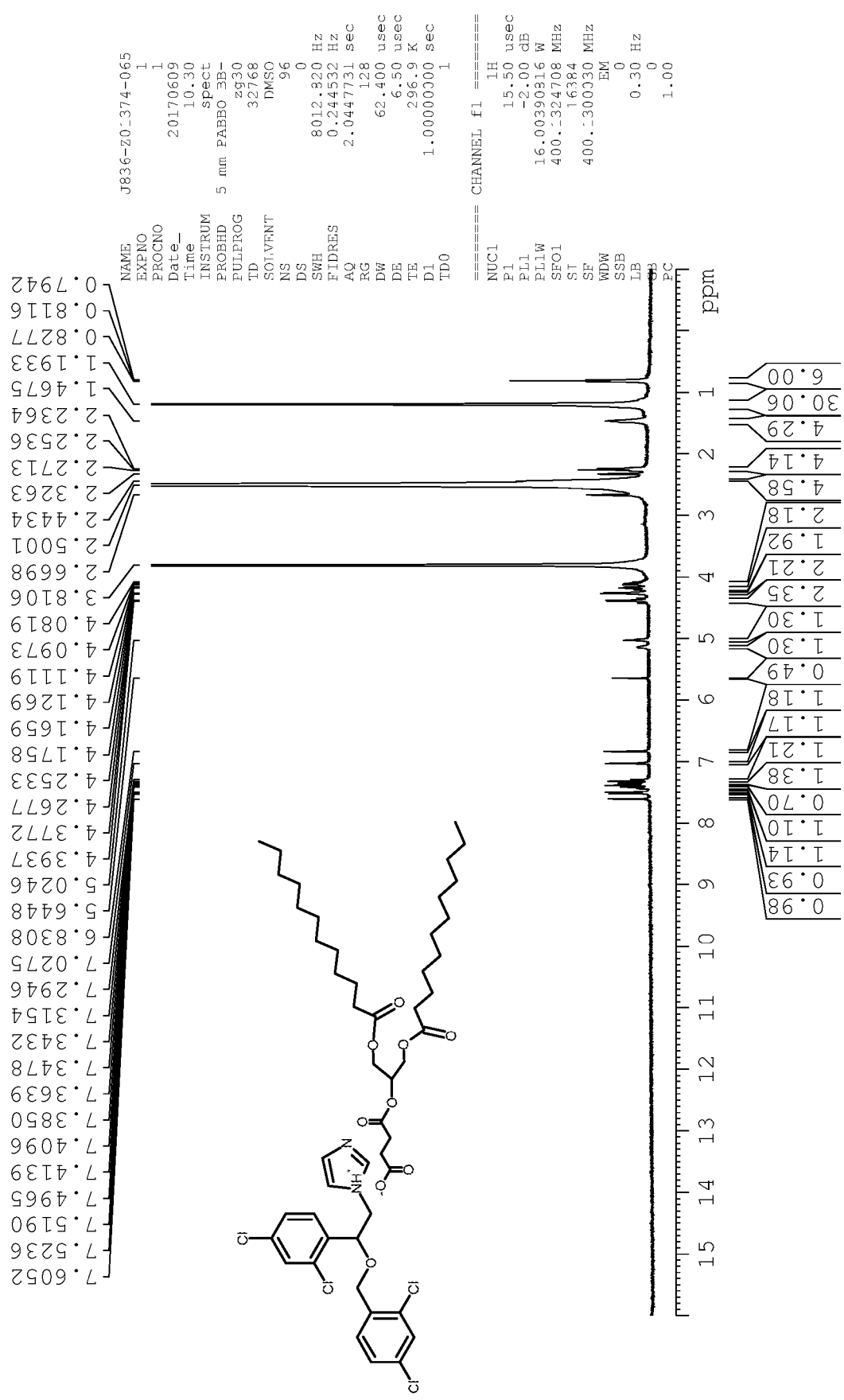
FIG. 1 shows an NMR spectra of compound 4-((1,3-bis(dodecanoyloxy)propan-2-yl)oxy)-4-oxobutanoate1-(2-((2,4-dichlorobenzyl)oxy)-2-(2,4-dichlorophenyl)ethyl)-1H-imidazol-1-ium 8.
Figure 2:
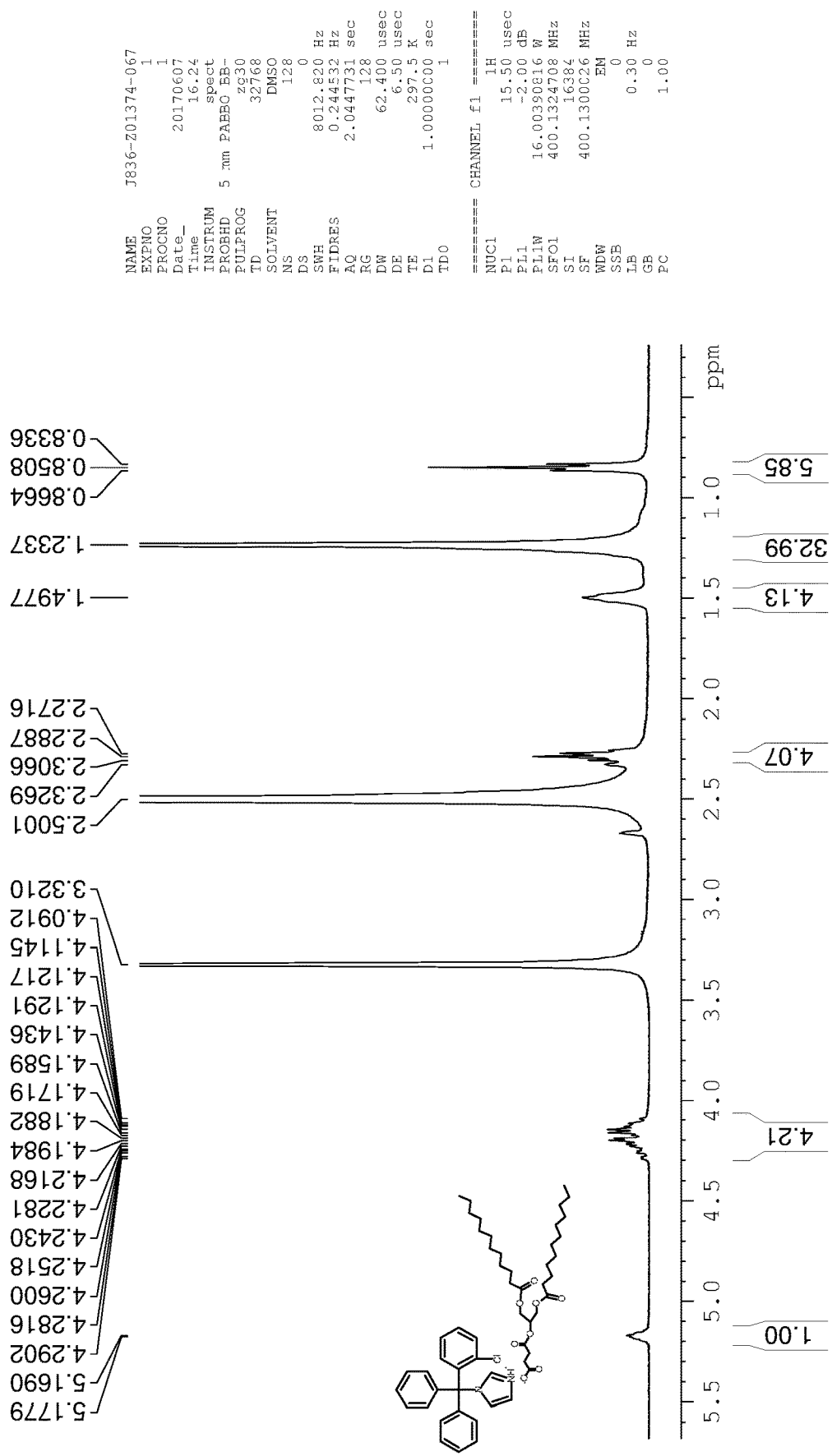
FIG. 2 shows an NMR spectra of compound 4-((1,3-bis(dodecanoyloxy)propan-2-yl)oxy)-4-oxobutanoate 1-((2-chlorophenyl)diphenylmethyl)-1H-imidazol-3-ium 10.
Figure 3:
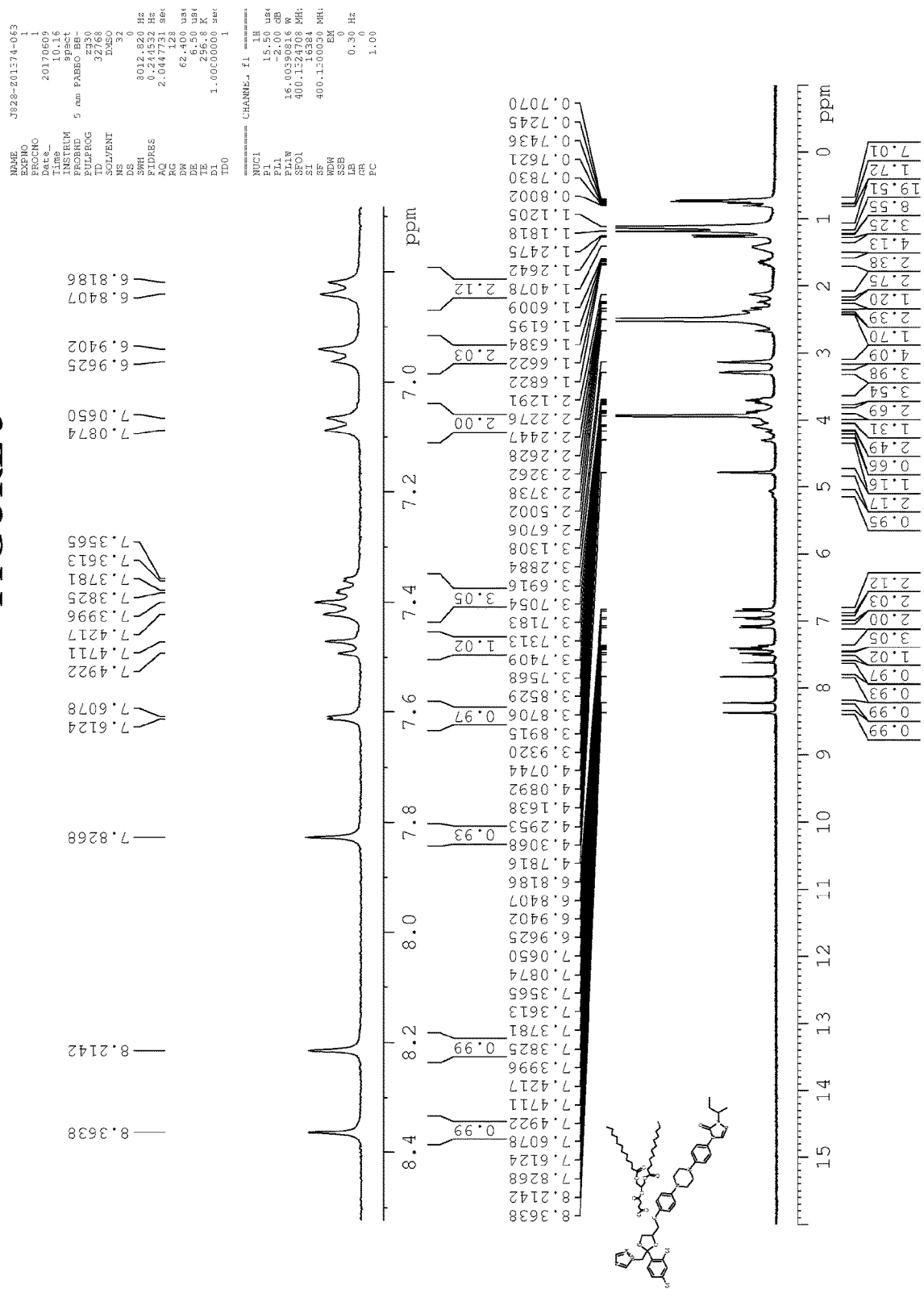
FIG. 3 shows an NMR spectra of compound 4-((1,3-bis(dodecanoyloxy)propan-2-yl)oxy)-4-oxobutanoate 1-((4-((4-(4-(4-(1-(sec-butyl)-5-oxo-1,5-dihydro-4H-1,2,4-triazol-4-yl)phenyl)piperazin-1-yl)phenoxy)methyl)-2-(2,4-dichlorophenyl)-1,3-dioxolan-2-yl)methyl)-1H-1,2,4-triazol-1-ium 12.
Figure 4:
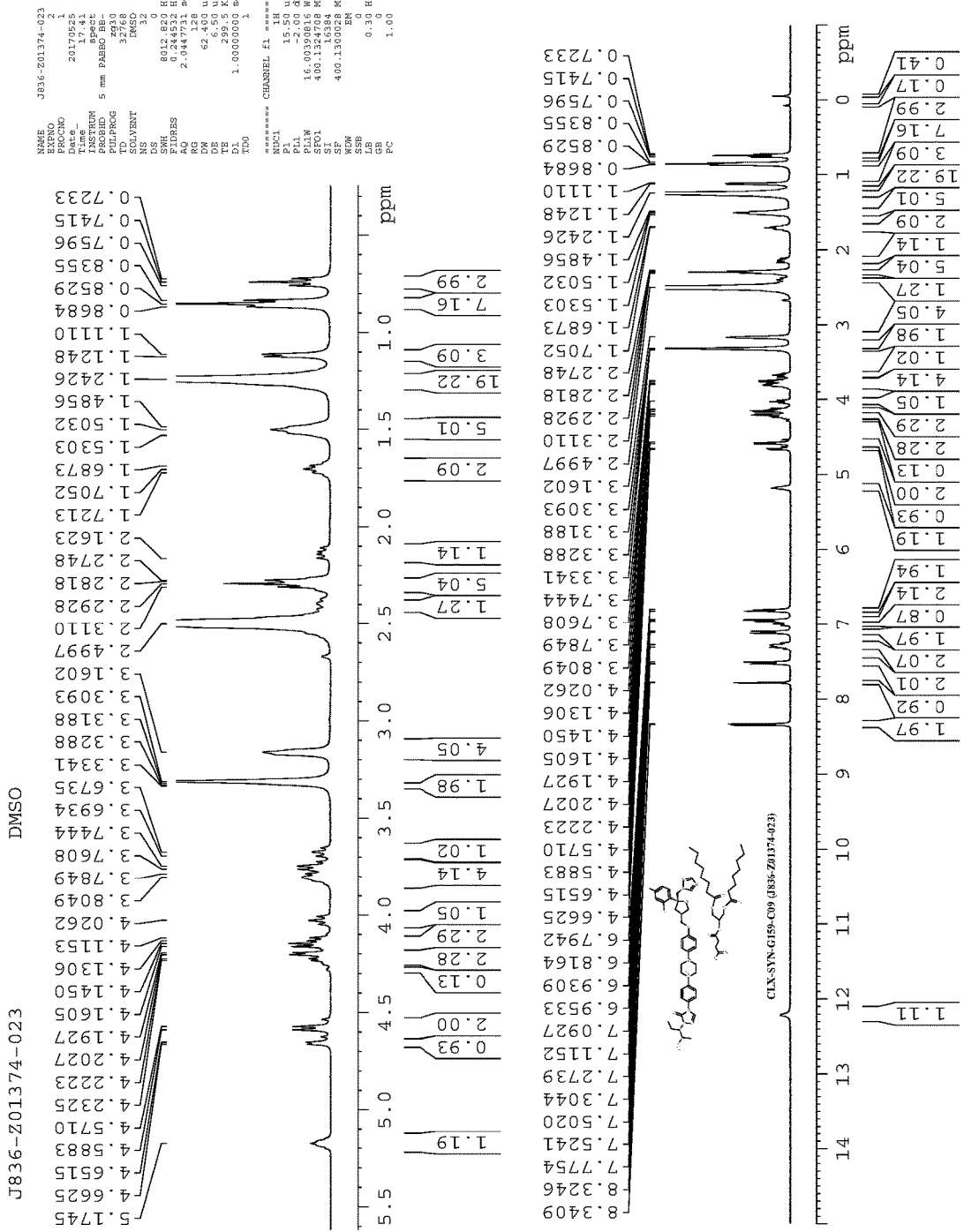
FIG. 4 shows an NMR spectra of compound 4-((1,3-bis(octanoyloxy)propan-2-yl)oxy)-4-oxobutanoate 4-(4-(((3R,5R)-5-((1H-1,2,4-triazol-1-yl)methyl)-5-(2,4-difluorophenyl)tetrahydrofuran-3-yl)methoxy)phenyl)-1-(4-(1-((2S,3S)-2-hydroxypentan-3-yl)-5-oxo-1,5-dihydro-4H-1,2,4-triazol-4-yl)phenyl)piperazin-1-ium 14.
Figure 5:
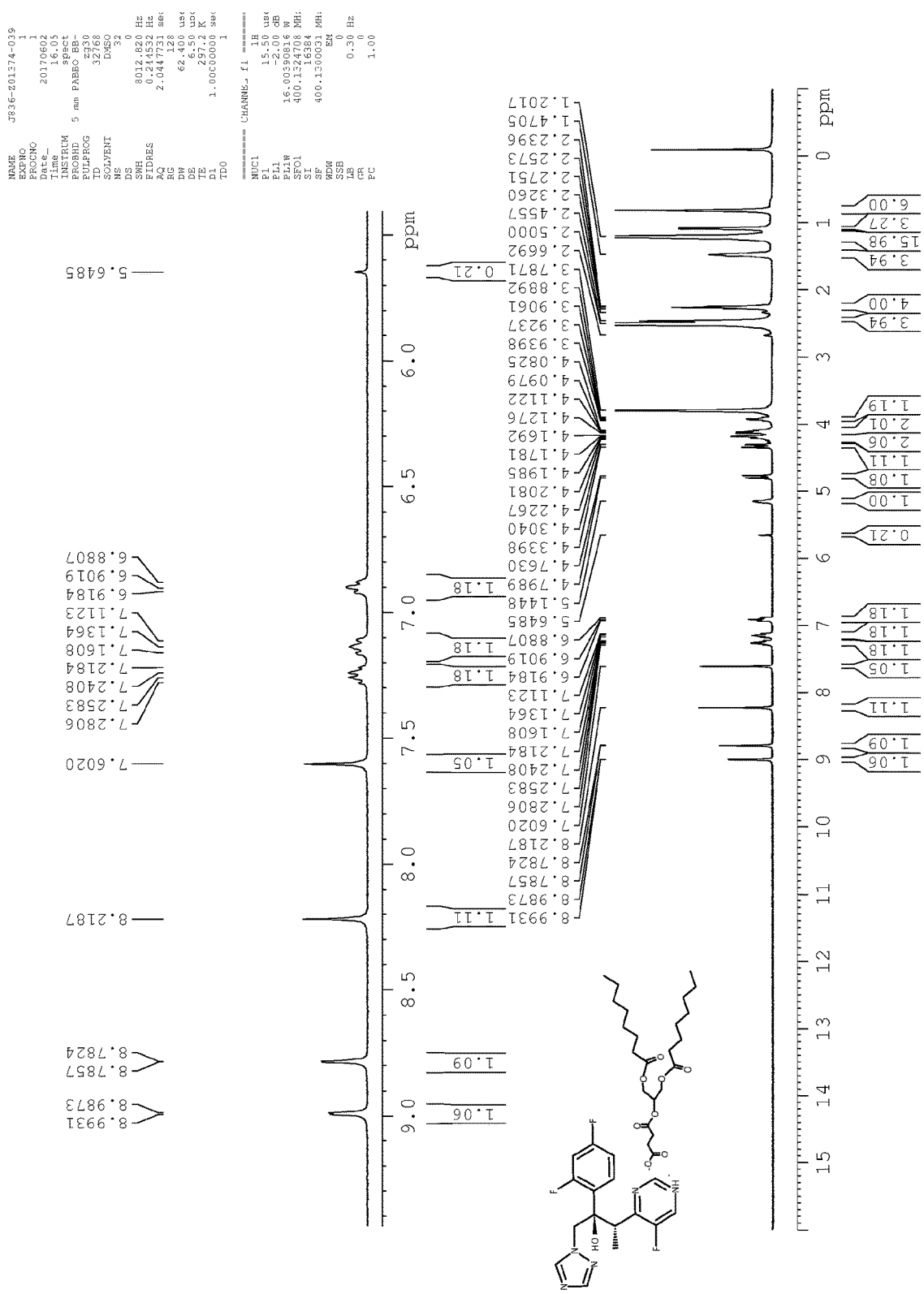
FIG. 5 shows an NMR spectra of compound 4-((1,3-bis(octanoyloxy)propan-2-yl)oxy)-4-oxobutanoate 4-((2S,3R)-3-(2,4-difluorophenyl)-3-hydroxy-4-(1H-1,2,4-triazol-1-yl)butan-2-yl)-5-fluoropyrimidin-1-ium 16.
Figure 6:
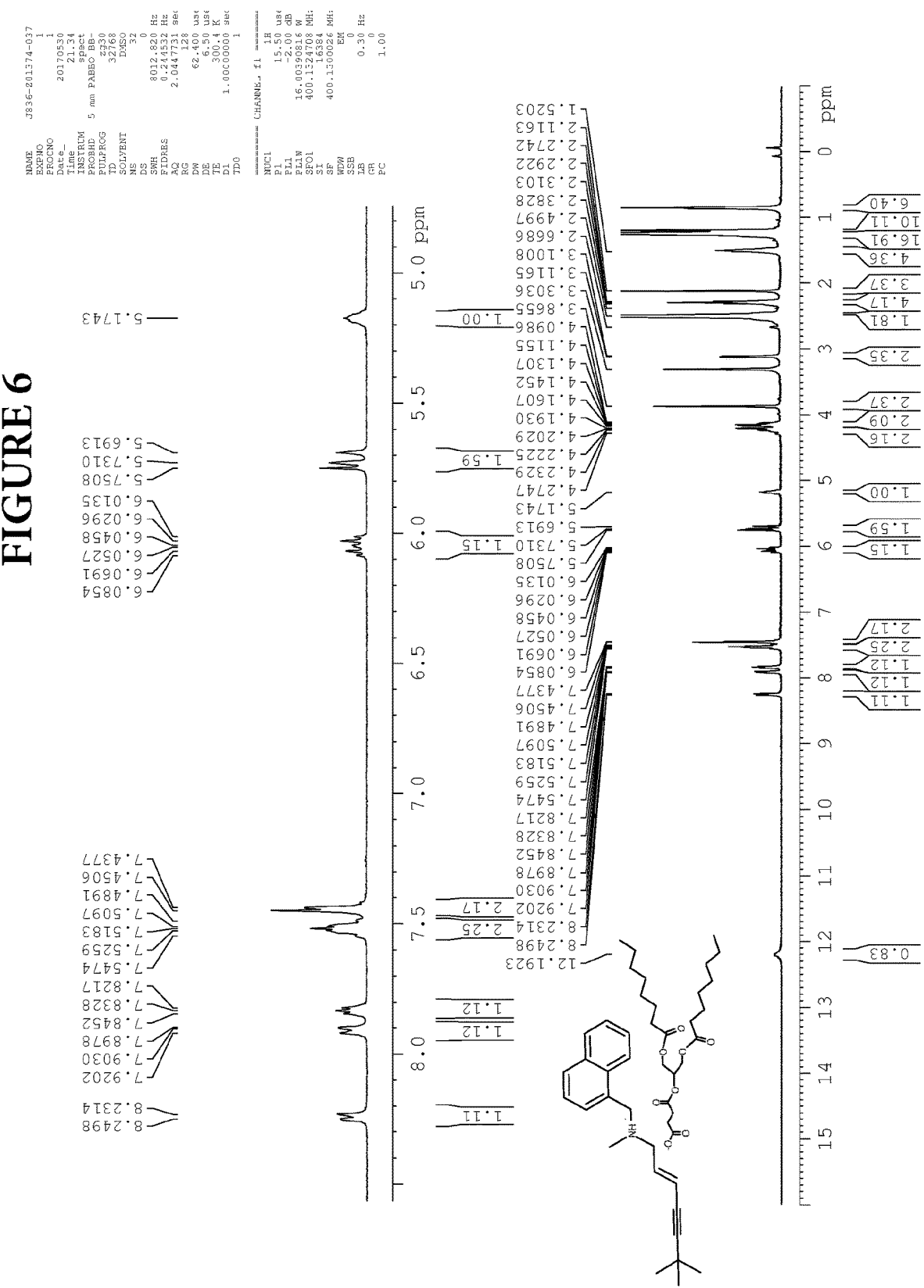
FIG. 6 shows an NMR spectra of compound 4-((1,3-bis(octanoyloxy)propan-2-yl)oxy)-4-oxobutanoate N,6,6-trimethyl-N-(naphthalene-1-ylmethyl)hept-2-en-4-yn-1-aminium 18.
Figure 7:
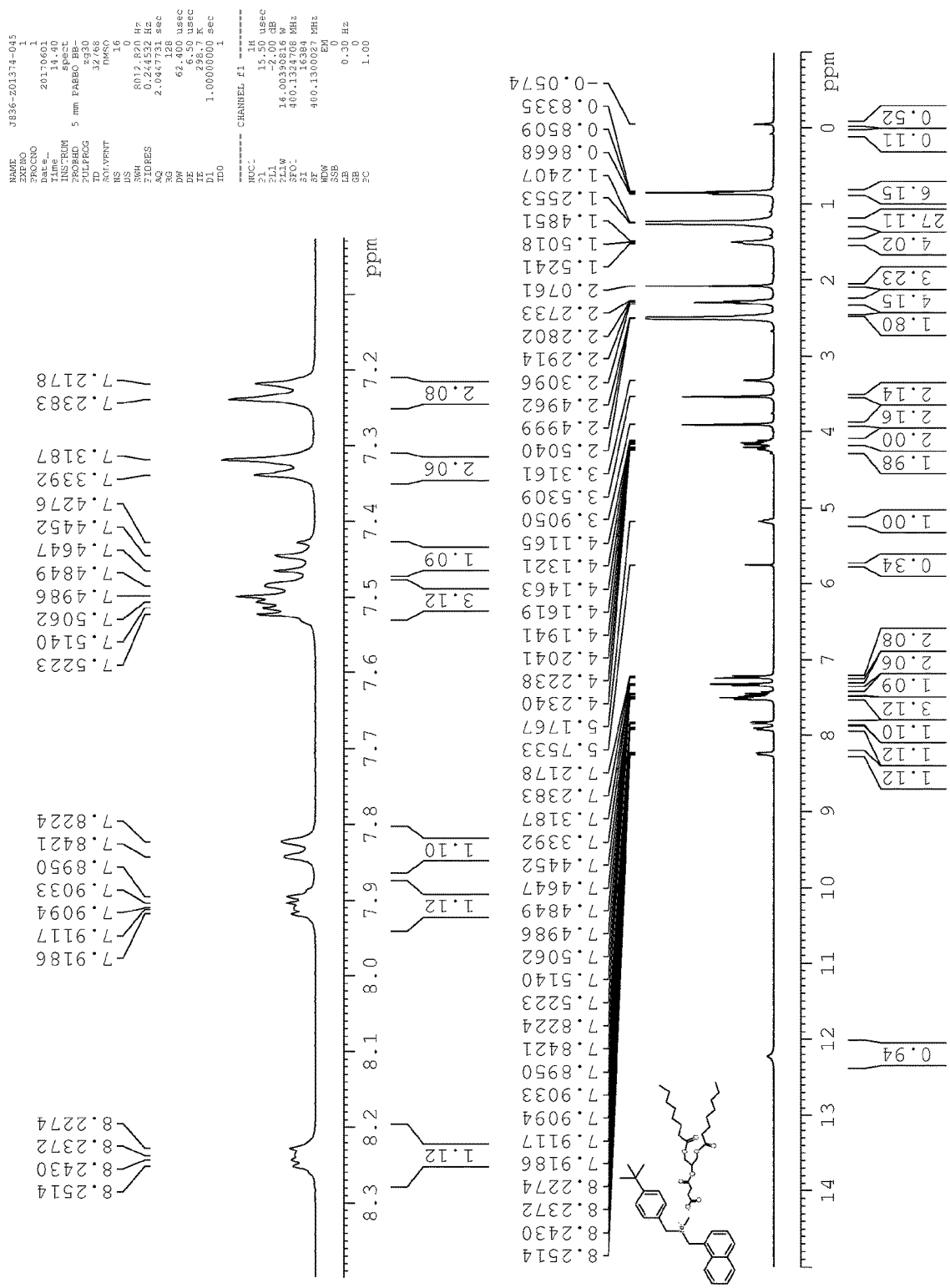
FIG. 7 shows an NMR spectra of compound 4-((1,3-bis(octanoyloxy)propan-2-yl)oxy)-4-oxobutanoate N-(4-(tert-butyl)benzyl)-N-methyl-1-(naphthalen-1-yl)methanaminium 20.
Figure 8:
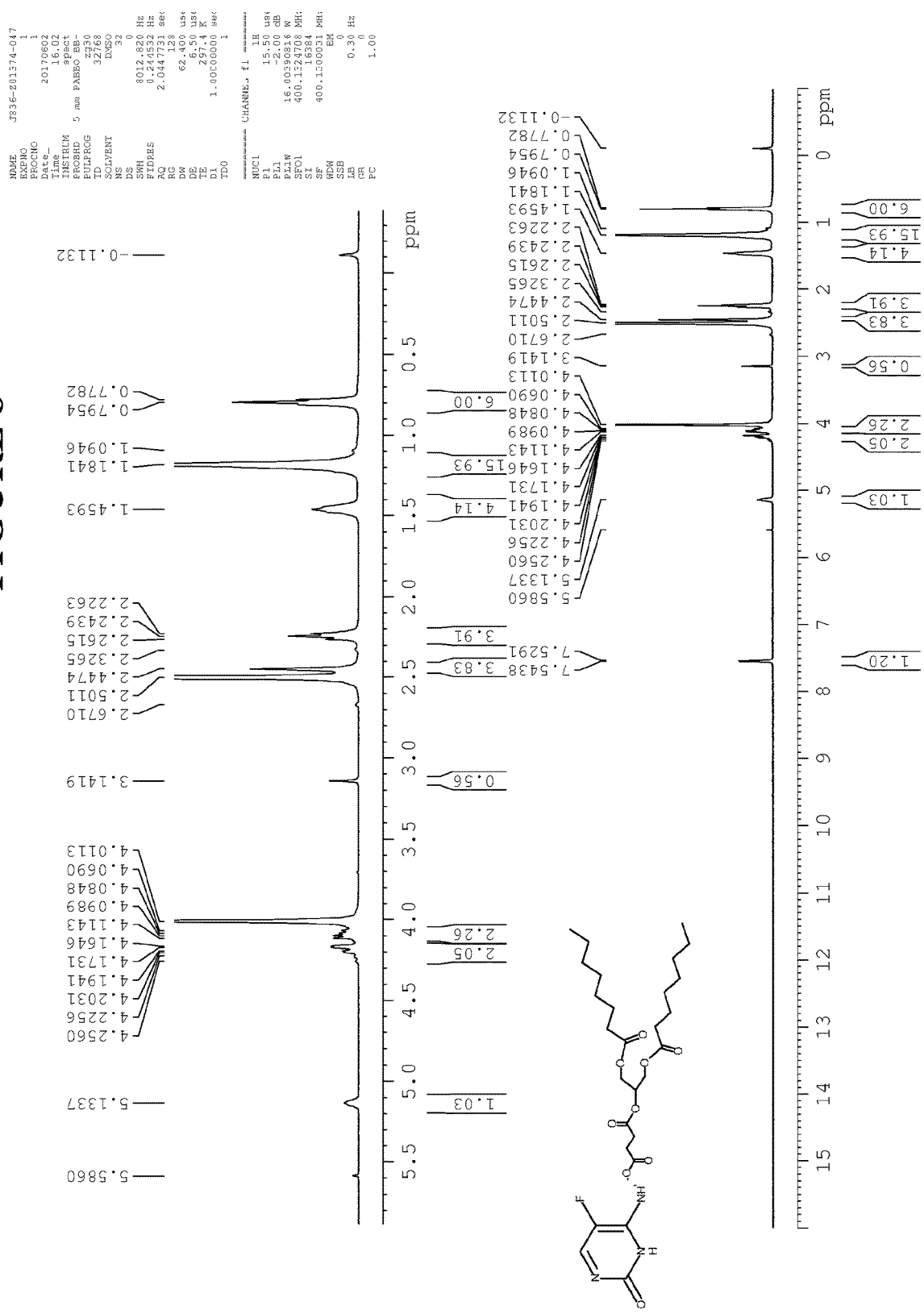
FIG. 8 shows an NMR spectra of compound 4-((1,3-bis(octanoyloxy)propan-2-yl)oxy)-4-oxobutanoate 5-fluoro-2-oxo-2,3-dihydropyrimidin-4-aminium 22.
Figure 9:
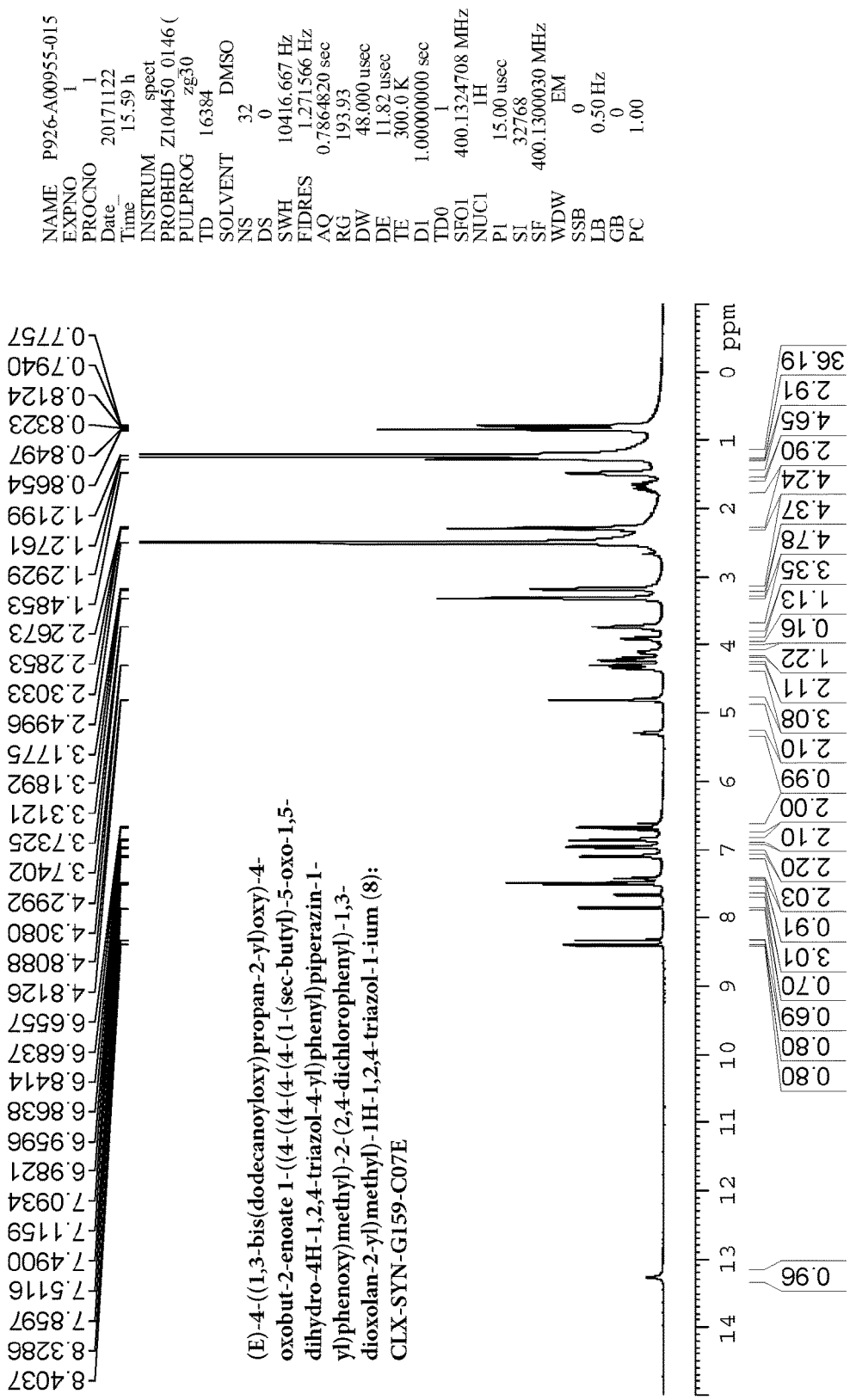
FIG. 9 shows an NMR spectra of compound (E)-4-((1,3-bis(dodecanoyloxy)propan-2-yl)oxy)-4-oxobut-2-enoate 1-((4-((4-(4-(1-(sec-butyl)-5-oxo-1,5-dihydro-4H-1,2,4-triazol-4-yl)phenyl)piperazin-1-yl)phenoxy)methyl)-2-(2,4-dichlorophenyl)-1,3-dioxolan-2-yl)methyl)-1H-1,2,4-triazol-1-ium (8).
Figure 10:
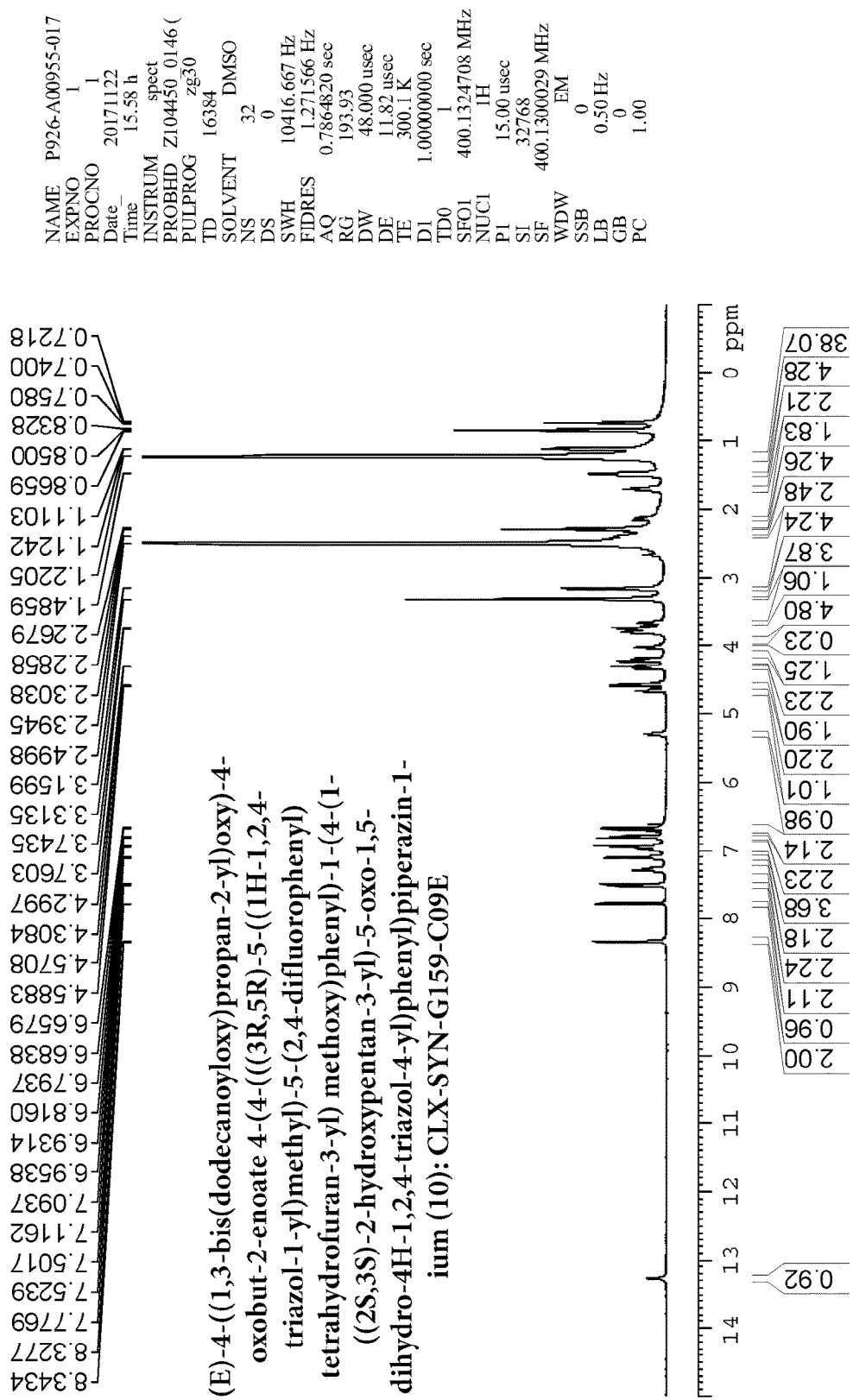
FIG. 10 shows an NMR spectra of compound (E)-4-((1,3-bis(dodecanoyloxy)propan-2-yl)oxy)-4-oxobut-2-enoate 4-(4-(((3R,5R)-5-((1H-1,2,4-triazol-1-yl)methyl)-5-(2,4-difluorophenyl)tetrahydrofuran-3-yl)methoxy)phenyl)-1-(4-(1-((2S,3S)-2-hydroxypentan-3-yl)-5-oxo-1,5-dihydro-4H-1,2,4-triazol-4-yl)phenyl)piperazin-1-ium(10): CLX-SYN-G159-C09E

As used herein, the following terms and phrases shall have the meanings set forth below. Unless defined otherwise, all technical and scientific terms used herein have the same meaning as commonly understood to one of ordinary skill in the art.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "metabolic condition" refers to an Inborn errors of metabolism (or genetic metabolic conditions) are genetic disorders that result from a defect in one or more metabolic pathways; specifically, the function of an enzyme is affected and is either deficient or completely absent.

The term "polymorph" as used herein is art-recognized and refers to one crystal structure of a given compound.

The phrases "parenteral administration" and "administered parenterally" as used herein refer to modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "predicting" as used herein refers to assessing the probability related diseases patient will suffer from abnormalities or complication and/or terminal platelet aggregation or failure and/or death (i.e. mortality) within a defined time window (predictive window) in the future. The mortality may be caused by the central nervous system or complication. The predictive window is an interval in which the subject will develop one or more of the said complications according to the predicted probability. The predictive window may be the entire remaining lifespan of the subject upon analysis by the method of the present invention.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating fungal infections, oral candidiasis, fungal infections, viral infections, bacterial infections, and other microbial related diseases or any other medical condition, is well understood in the art, and includes administration of a composition which reduces the frequency of, or delays the onset of, symptoms of a medical condition in a subject relative to a subject which does not receive the composition.

The phrase "therapeutically effective amount" is an art-recognized term. In certain embodiments, the term refers to an amount of a solvate or hydrate or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

In certain embodiments, the pharmaceutical compositions described herein are formulated in a manner such that said compositions will be delivered to a patient in a therapeutically effective amount, as part of a prophylactic or therapeutic treatment. The desired amount of the composition to be administered to a patient will depend on absorption, inactivation, and excretion rates of the drug as well as the delivery rate of the hydrates or solvates and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular solvate or hydrate or composition may be adjusted to accommodate variations in the treatment parameters. Such treatment parameters include the clinical use to which the preparation is put, e.g., the site treated, the type of patient, e.g., human or non-human, adult or child, and the nature of the disease or condition.

In certain embodiments, the dosage of the subject compositions provided herein may be determined by reference to the plasma concentrations of the therapeutic composition or other encapsulated materials. For example, the maximum plasma concentration (C max) and the area under the plasma concentration-time curve from time 0 to infinity may be used.

When used with respect to a pharmaceutical composition or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active solvate or hydrate and/or composition, for a sustained or extended period (as compared to the release from a bolus). This release may result in prolonged delivery of therapeutically effective amounts of any of the therapeutic agents disclosed herein.

The phrases "systemic administration," "administered systemically," "peripheral administration" and "administered peripherally" are art-recognized, and include the administration of a subject composition, therapeutic or other material at a site remote from the disease being treated. Administration of an agent for the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of a solvate or hydrate or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The present disclosure also contemplates prodrugs of the compositions disclosed herein, as well as pharmaceutically acceptable hydrates or solvates of said prodrugs.

This application also discloses a pharmaceutical composition comprising a pharmaceutically acceptable carrier and the composition of a compound of formula I, formula II, formula III, formula IV, formula V, formula VI, formula VII, formula VIII, formula IX or Formula X may be formulated for systemic or topical or oral administration. The pharmaceutical composition may be also formulated for oral administration, oral solution, injection, subdermal administration, or transdermal administration. The pharmaceutical composition may further comprise at least one of a pharmaceutically acceptable stabilizer, diluent, surfactant, filler, binder, and lubricant.

In many embodiments, the pharmaceutical compositions described herein will incorporate the disclosed compounds and compositions (formula I, formula II, formula III, formula IV, formula V, formula VI, formula VII, formula VIII, formula IX, formula X to be delivered in an amount sufficient to deliver to a patient a therapeutically effective amount of a compound of formula I, formula II, formula III, formula IV, formula V, formula VI, formula VII, formula VIII, formula IX or Formula X or composition as part of a prophylactic or therapeutic treatment. The desired concentration of formula I, formula II, formula III, formula IV, formula V, formula VI, formula VII, formula VIII, formula IX or Formula X or its pharmaceutical acceptable hydrates or solvates will depend on absorption, inactivation, and excretion rates of the drug as well as the delivery rate of the hydrates or solvates and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular compound of formula I, formula II, formula III, formula IV, formula V, formula VI, formula VII, formula VIII, formula IX or Formula X may be adjusted to accommodate variations in the treatment parameters. Such treatment parameters include the clinical use to which the preparation is put, e.g., the site treated, the type of patient, e.g., human or non-human, adult or child, and the nature of the disease or condition.

The concentration and/or amount of any compound of formula I, formula II, formula III, formula IV, formula V, formula VI, formula VII, formula VIII, formula IX or Formula X may be readily identified by routine screening in animals, e.g., rats, by screening a range of concentration and/or amounts of the material in question using appropriate assays. Known methods are also available to assay local tissue concentrations, diffusion rates of the hydrates or solvates or compositions, and local blood flow before and after administration of therapeutic formulations disclosed herein. One such method is microdialysis, as reviewed by T. E. Robinson et al., 1991, microdialysis in the neurosciences, Techniques, volume 7, Chapter 1. The methods reviewed by Robinson may be applied, in brief, as follows. A microdialysis loop is placed in situ in a test animal. Dialysis fluid is pumped through the loop. When compounds with formula I, formula II, formula III, formula IV, formula V, formula VI, formula VII, formula VIII, formula IX or Formula X such as those disclosed herein are injected adjacent to the loop, released drugs are collected in the dialysate in proportion to their local tissue concentrations. The progress of diffusion of the hydrates or solvates or compositions may be determined thereby with suitable calibration procedures using known concentrations of hydrates or solvates or compositions.

In certain embodiments, the dosage of the subject compounds of formula I, formula II, formula III, formula IV, formula V, formula VI, formula VII, formula VIII, formula IX or Formula X provided herein may be determined by reference to the plasma concentrations of the therapeutic composition or other encapsulated materials. For example, the maximum plasma concentration (C max) and the area under the plasma concentration-time curve from time 0 to infinity may be used.

Generally, in carrying out the methods detailed in this application, an effective dosage for the compounds of formula I, formula II, formula III, formula IV, formula V, formula VI, formula VII, formula VIII, formula IX or Formula X is in the range of about 0.01 mg/kg/day to about 100 mg/kg/day in single or divided doses, for instance 0.01 mg/kg/day to about 50 mg/kg/day in single or divided doses. The compounds of Formulas I may be administered at a dose of, for example, less than 0.2 mg/kg/day, 0.5 mg/kg/day, 1.0 mg/kg/day, 5 mg/kg/day, 10 mg/kg/day, 20 mg/kg/day, 30 mg/kg/day, or 40 mg/kg/day. Compounds of formula I, formula II, formula III, formula IV, formula V, formula VI, formula VII, formula VIII, formula IX or Formula X may also be administered to a human patient at a dose of, for example, between 0.1 mg and 1000 mg, between 5 mg and 80 mg, or less than 1.0, 9.0, 12.0, 20.0, 50.0, 75.0, 100, 300, 400, 500, 800, 1000, 2000, 5000 mg per day. In certain embodiments, the compositions herein are administered at an amount that is less than 95%, 90%, 80%, 70%, 60%, 50%, 40%, 30%, 20%, or 10% of the compound of formula I, formula II, formula III, formula IV, formula V, formula VI, formula VII, formula VIII, formula IX or Formula X required for the same therapeutic benefit.

An effective amount of the compounds of formula I, formula II, formula III, formula IV, formula V, formula VI, formula VII, formula VIII, formula IX or Formula X described herein refers to the amount of one of said hydrates or solvates or compositions which is capable of inhibiting or preventing a disease.

An effective amount may be sufficient to prohibit, treat, alleviate, ameliorate, halt, restrain, slow or reverse the progression, or reduce the severity of a complication resulting from nerve damage or demyelization and/or elevated reactive oxidative-nitrosative species and/or abnormalities in neurotransmitter homeostasis's, in patients who are at risk for such complications. As such, these methods include both medical therapeutic (acute) and/or prophylactic (prevention) administration as appropriate. The amount and timing of compositions administered will, of course, be dependent on the subject being treated, on the severity of the affliction, on the manner of administration and on the judgment of the prescribing physician. Thus, because of patient-to-patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

The compositions provided by this application may be administered to a subject in need of treatment by a variety of conventional routes of administration, including orally, topically, parenterally, e.g., intravenously, subcutaneously or intramedullary. Further, the compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

The compositions may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compositions and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as L-arginine, sodium citrate, calcium carbonate and calcium phosphate may be employed along with various disintegrates such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Appropriate materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof. The compounds of formula I, formula II, formula III, formula IV, formula V, formula VI, formula VII, formula VIII, formula IX or formula X may also comprise enterically coated comprising of various excipients, as is well known in the pharmaceutical art.

For parenteral administration, solutions of the compositions may be prepared in (for example) sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The formulations, for instance tablets, may contain e.g. 10 to 100, 50 to 250, 150 to 500 mg, or 350 to 800 mg e.g. 10, 50, 100, 300, 500, 700, 800 mg of the compounds of formula I, formula II, formula III, formula IV, formula V, formula VI, formula VII, formula VIII, formula IX or Formula X disclosed herein, for instance, compounds of formula I, formula II, formula III, formula IV, formula V, formula VI, formula VII, formula VIII, formula IX or Formula X or pharmaceutical acceptable hydrates or solvates of a compounds of formula I, formula II, formula III, formula IV, formula V, formula VI, formula VII, formula VIII, formula IX or Formula X.

Generally, a composition as described herein may be administered orally, or parenterally (e.g., intravenous, intramuscular, subcutaneous or intramedullary). Topical administration may also be indicated, for example, where the patient is suffering from gastrointestinal disorder that prevent oral administration, or whenever the medication is best applied to the surface of a tissue or organ as determined by the attending physician. Localized administration may also be indicated, for example, when a high dose is desired at the target tissue or organ. For buccal administration the active composition may take the form of tablets or lozenges formulated in a conventional manner.

The dosage administered will be dependent upon the identity of the neurological disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. For oral administration either solid or fluid unit dosage forms can be prepared.

As discussed above, the tablet core contains one or more hydrophilic polymers. Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, high-molecular weight crosslinked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

The carrier may contain one or more suitable excipients for the formulation of tablets. Examples of suitable excipients include, but are not limited to, fillers, adsorbents, binders, disintegrants, lubricants, glidants, release-modifying excipients, superdisintegrants, antioxidants, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their hydrates or solvates, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their hydrates or solvates, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the tablet core contains up to about 5 percent by weight of such super disintegrant.

Examples of antioxidants include, but are not limited to, tocopherols, ascorbic acid, sodium pyrosulfite, butylhydroxytoluene, butylated hydroxyanisole, edetic acid, and edetate hydrates or solvates, and mixtures thereof. Examples of preservatives include, but are not limited to, citric acid, tartaric acid, lactic acid, malic acid, acetic acid, benzoic acid, and sorbic acid, and mixtures thereof.

In one embodiment, the immediate release coating has an average thickness of at least 50 microns, such as from about 50 microns to about 2500 microns; e.g., from about 250 microns to about 1000 microns. In embodiment, the immediate release coating is typically compressed at a density of more than about 0.9 g/cc, as measured by the weight and volume of that specific layer.

In one embodiment, the immediate release coating contains a first portion and a second portion, wherein at least one of the portions contains the second pharmaceutically active agent. In one embodiment, the portions contact each other at a center axis of the tablet. In one embodiment, the first portion includes the first pharmaceutically active agent and the second portion includes the second pharmaceutically active agent.

In one embodiment, the first portion contains the first pharmaceutically active agent and the second portion contains the second pharmaceutically active agent. In one embodiment, one of the portions contains a third pharmaceutically active agent. In one embodiment one of the portions contains a second immediate release portion of the same pharmaceutically active agent as that contained in the tablet core.

In one embodiment, the outer coating portion is prepared as a dry blend of materials prior to addition to the coated tablet core. In another embodiment the outer coating portion is included of a dried granulation including the pharmaceutically active agent.

Formulations with different drug release mechanisms described above could be combined in a final dosage form containing single or multiple units. Examples of multiple units include multilayer tablets, capsules containing tablets, beads, or granules in a solid or liquid form. Typical, immediate release formulations include compressed tablets, gels, films, coatings, liquids and particles that can be encapsulated, for example, in a gelatin capsule. Many methods for preparing coatings, covering or incorporating drugs, are known in the art.

The immediate release dosage, unit of the dosage form, i.e., a tablet, a plurality of drug-containing beads, granules or particles, or an outer layer of a coated core dosage form, contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads).

Extended release formulations are generally prepared as diffusion or osmotic systems, for example, as described in "Remington—The Science and Practice of Pharmacy", 20th. Ed., Lippincott Williams & Wilkins, Baltimore, Md., 2000). A diffusion system typically consists of one of two types of devices, reservoir and matrix, which are wellknown and described in die art. The matrix devices are generally prepared by compressing the drug with a slowly dissolving polymer carrier into a tablet form.

An immediate release portion can be added to the extended release system by means of either applying an immediate release layer on top of the extended release core; using coating or compression processes or in a multiple unit system such as a capsule containing extended and immediate release beads.

Delayed release dosage formulations are created by coating a solid dosage form with a film of a polymer which is insoluble in the acid environment of the stomach, but soluble in the neutral environment of small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule.

A pulsed release dosage form is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

Each dosage form contains a therapeutically effective amount of active agent. In one embodiment of dosage forms that mimic a twice daily dosing profile, approximately 30 wt. % to 70 wt. %, preferably 40 wt. % to 60 wt. %, of the total amount of active agent in the dosage form is released in the initial pulse, and, correspondingly approximately 70 wt. % to 3.0 wt. %, preferably 60 wt. % to 40 wt. %, of the total amount of active agent in the dosage form is released in the second pulse. For dosage forms mimicking the twice daily dosing profile, the second pulse is preferably released approximately 3 hours to less than 14 hours, and more preferably approximately 5 hours to 12 hours, following administration.

Another dosage form contains a compressed tablet or a capsule having a drug-containing immediate release dosage unit, a delayed release dosage unit and an optional second delayed release dosage unit. In this dosage form, the immediate release dosage unit contains a plurality of beads, granules particles that release drug substantially immediately following oral administration to provide an initial dose. The delayed release dosage unit contains a plurality of coated beads or granules, which release drug approximately 3 hours to 14 hours following oral administration to provide a second dose.

For purposes of transdermal (e.g., topical) administration, dilute sterile, aqueous or partially aqueous solutions (usually in about 0.1% to 5% concentration), otherwise similar to the above parenteral solutions, may be prepared.

Methods of preparing various pharmaceutical compositions with a certain amount of one or more compounds of formula I, formula II, formula III, formula IV, formula V, formula VI, formula VII, formula VIII, formula IX, formula X, or other active agents are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In addition, in certain embodiments, subject compositions of the present application maybe lyophilized or subjected to another appropriate drying technique such as spray drying.

The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

Methods of preparing these formulations or compositions include the step of bringing into association subject compositions with the carrier and, optionally, one or more accessory ingredients. In general, the formulations are prepared by uniformly and intimately bringing into association a subject composition with liquid carriers, or finely divided solid carriers, or both, and then, if necessary, shaping the product.

The compounds of formula I, formula II, formula III, formula IV, formula V, formula VI, formula VII, formula VIII, formula IX or Formula X described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the subject compositions, may contain suspending agents such as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

In another embodiment, a transdermal patch may comprise: a substrate sheet comprising a composite film formed of a resin composition comprising 100 parts by weight of a polyvinyl chloride-polyurethane composite and 2-10 parts by weight of a styrene-ethylene-butylene-styrene copolymer, a first adhesive layer on the one side of the composite film, and a polyalkylene terephthalate film adhered to the one side of the composite film by means of the first adhesive layer, a primer layer which comprises a saturated polyester resin and is formed on the surface of the polyalkylene terephthalate film; and a second adhesive layer comprising a styrene-diene-styrene block copolymer containing a pharmaceutical agent layered on the primer layer.

Transdermal patches may be passive or active. Passive transdermal drug delivery systems currently available, such as the nicotine, estrogen and nitroglycerine patches, deliver small-molecule drugs. Many of the newly developed proteins and peptide drugs are too large to be delivered through passive transdermal patches and may be delivered using technology such as electrical assist (iontophoresis) for large-molecule drugs.

Iontophoresis is a technique employed for enhancing the flux of ionized substances through membranes by application of electric current. One example of an iontophoretic membrane is given in U.S. Pat. No. 5,080,646 to Theeuwes. The principal mechanisms by which iontophoresis enhances molecular transport across the skin are (a) repelling a charged ion from an electrode of the same charge, (b) electroosmosis, the convective movement of solvent that occurs through a charged pore in response the preferential passage of counter-ions when an electric field is applied or (c) increase skin permeability due to application of electrical current.

Methods and compositions for the treatment of oral infectious diseases. Among other things, herein is provided a method of treating oral infectious diseases, comprising administering to a patient in need thereof a therapeutically effective amount of compound of Formula's in the specification as a general scheme for acid part [6] & [6A] synthesis and formula I, formula II, formula III, formula IV, formula V, formula VI, formula VII, formula VIII, formula IX or Formula X:

General Scheme for Acid Part (6) Synthesis:

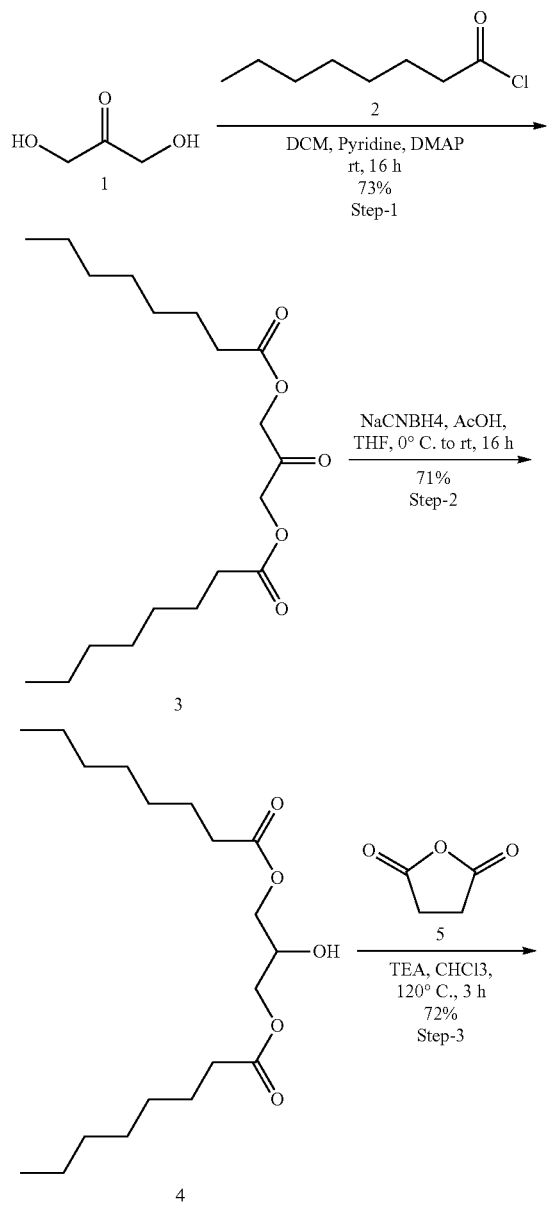

-continued

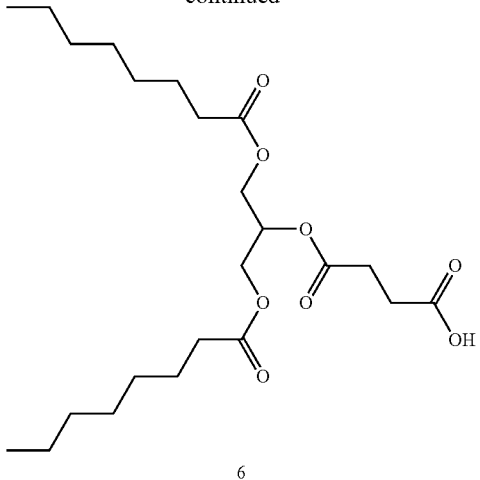

Synthesis of 2-oxopropane-1,3-diyl dioctanoate (3): To an ice cold solution of 1,3-dihydroxypropan-2-one (1, 25.0 g, 0.277 mol) in dichloromethane (500 mL) was added 4-dimethylaminopyridine (10.17 g, 0.083 mol) and pyridine (49.2 mL, 0.610 mol) and stirred for next 5 min. To the above mixture octanoyl chloride (2, 105.4 mL, 0.610 mol) was added dropwise at 0° C. and the reaction mixture was stirred at room temperature for 16 h. After completion, reaction mixture was filtered; the solid was washed with dichloromethane (100 mL), filtrate was washed with brine (200 mL), saturated solution of sodium bicarbonate (200 mL) and 0.1 N HCl solution (100 mL). Organic layer was separated and dried over anhydrous sodium sulfate and solvent was removed under reduced pressure to get crude. The crude was purified by silica gel (100-200 mesh) column chromatography eluting with 10% ethyl acetate in hexanes to afford the desired product as white solid. Yield: 70.0 g, 73%.

MS (ESI) m/z 343.19[M+1]$^+$;

$^1$H NMR (400 MHz, DMSO-d6); δ 4.84 (s, 4H), 2.37 (t, J=7.2 Hz, 4H), 1.45-1.62 (m, 4H), 1.15-1.35 (m, 16H), 0.78-0.92 (m, 6H).

Synthesis of 2-hydroxypropane-1,3-diyl dioctanoate (4): To an ice cold solution of 2-oxopropane-1,3-diyl dioctanoate (3, 70.0 g, 0.204 mol) in THF (1000 mL) was added drop wise acetic acid (15 mL) followed by the portion wise addition of sodium cyanoborohydride (15.43 g, 0.245 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude thus obtained was purified by silica gel (100-200 mesh) column chromatography eluting with 12 to 15% ethyl acetate in hexanes to afford the desired product 4 as yellow liquid. Yield: 50.0 g, 71%.

MS (ESI) m/z 345.29[M+1]$^+$;

$^1$H NMR (400 MHz, DMSO-d6): δ 5.25 (d, J=5.2 Hz, 1H), 3.92-4.03 (m, 4H), 3.81-3.90 (m, 1H), 2.29 (t, J=7.6 Hz, 4H), 1.45-1.59 (m, 4H), 1.12-1.35 (m, 16H), 0.85 (t, J=6.8 Hz, 6H).

Synthesis of 4-((1,3-bis(octanoyloxy)propan-2-yl)oxy)-4-oxobutanoic acid (6): To a solution of 2-hydroxypropane-1,3-diyl dioctanoate (4, 50.0 g, 0.145 mol) in chloroform (200 mL), dihydrofuran-2,5-dione (5, 17.44 g, 0.174 mol) and triethylamine (30.0 mL, 0.218 mol) were added at room temperature. The reaction mixture was stirred at 120° C. for 3 h. After completion, reaction mixture was diluted with water (200 mL) and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 10 to 15% ethyl acetate in hexanes to affored the desired product 6 as white solid. Yield: 47.0 g, 72%.

MS (ESI) m/z 443.2[M−1];

$^1$H NMR (400 MHz, DMSO-d6): δ 12.22 (s, 1H), 5.12-5.22 (m, 1H), 4.18-4.25 (m, 2H), 4.09-4.17 (m, 2H), 2.42-2.50 (m, 4H), 2.29 (t, J=7.24 Hz, 4H), 1.44-1.55 (m, 4H), 1.15-1.31 (m, 16H), 0.79-0.90 (m, 6H).

General Scheme for Acid Part (6A) Synthesis:

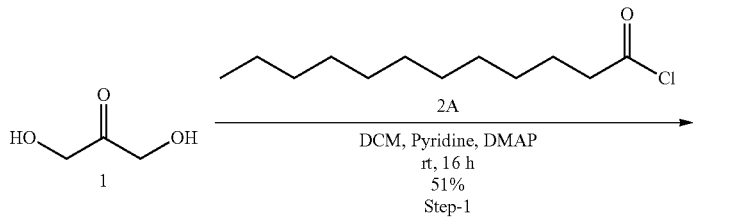

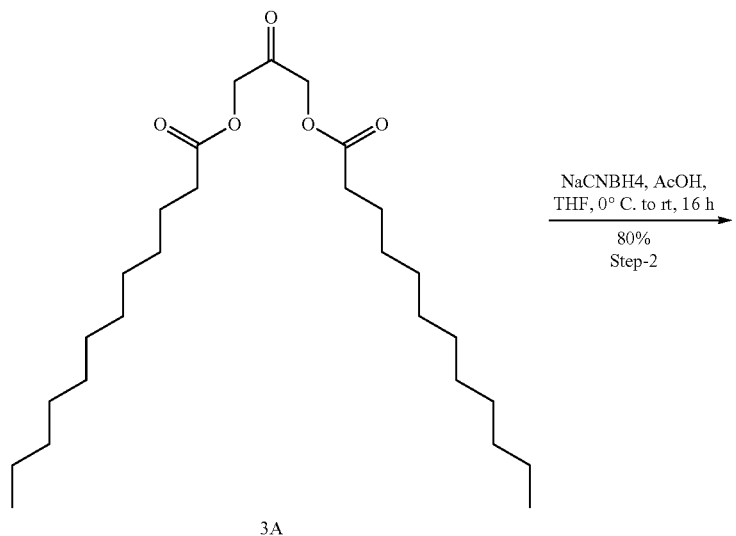

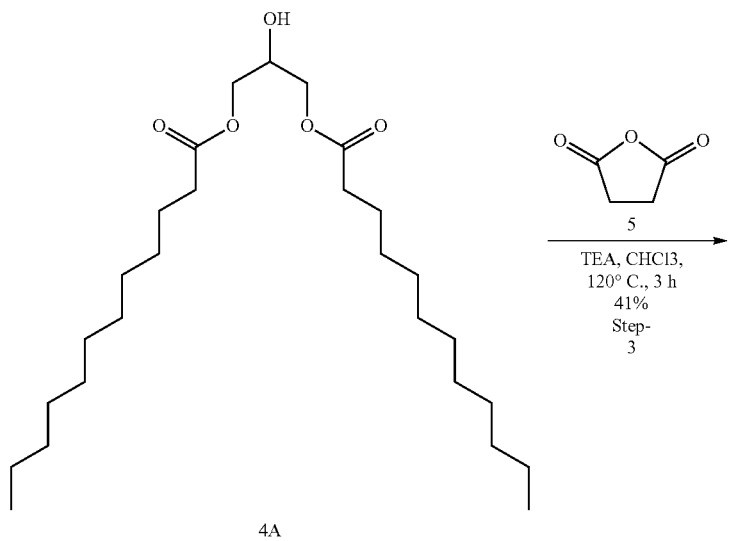

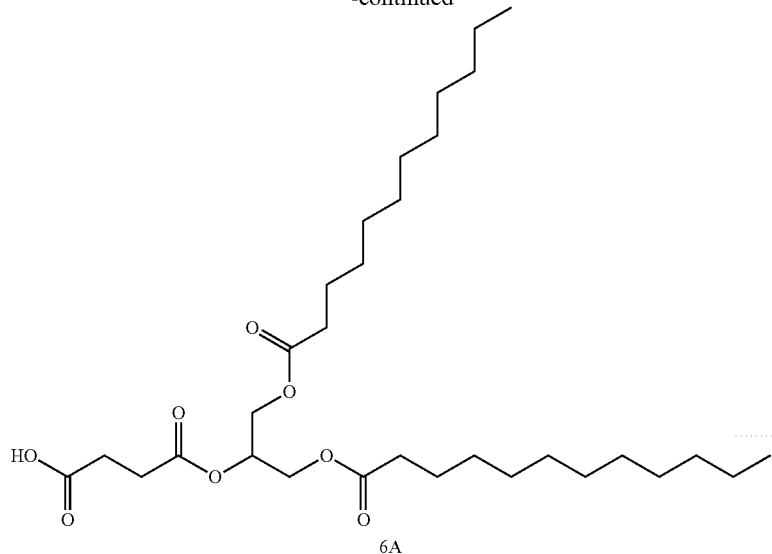

6A

Synthesis of 2-oxopropane-1,3-diyl didodecanoate (3A): To an ice cold solution of 1,3-dihydroxypropan-2-one (1, 30.0 g, 0.33 mol) in dichloromethane (500 mL) was added 4-dimethylaminopyridine (20.30 g, 0.167 mol) and pyridine (107 mL, 0.1.332 mol) and stirred for next 5 min. To the above mixture dodecanoyl chloride 2A (218.50 g, 1.167 mol) was added dropwise at 0° C. and the reaction mixture was stirred at room temperature for 16 h. After completion, reaction mixture was filtered; the solid was washed with dichloromethane (100 mL), filtrate was washed with brine (200 mL), saturated solution of sodium bicarbonate (200 mL) and 0.1 N HCl solution (100 mL). Organic layer was separated and dried over anhydrous sodium sulfate and solvent was removed under reduced pressure to get crude. The crude was triturated with diethyl ether to afford the desired product 3A as white solid. Yield: 78 g, 51%.

MS (ESI) m/z 455.37[M+1]$^+$;

$^1$H NMR (400 MHz, DMSO-d6); δ 4.74 (s, 4H), 2.43 (m, 4H), 1.64 (m, 4H), 1.55-1.25 (m, 32H), 0.87 (m, 6H).

Synthesis of 2-hydroxypropane-1,3-diyl didodecanoate (4A): To an ice cold solution of 2-oxopropane-1,3-diyl didodecanoate 3A (75.0 g, 0.165 mol) in THF (1000 mL) was added drop wise acetic acid (15 mL) followed by the portion wise addition of sodium cyanoborohydride (12.41 g, 0.198 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude was triturated with diethyl ether to afford the desired product 4A as white solid. Yield: 60.0 g, 80%.

MS (ESI) m/z 457.48[M+1]$^+$;

$^1$H NMR (400 MHz, DMSO-d6); δ 5.26 (d, J=5.2 Hz, 1H), 3.92-3.98 (m, 4H), 2.28 (m, 4H), 1.50 (m, 4H), 1.23 (m, 33H), 0.83 (m, 6H).

Synthesis of 4-((1,3-bis(dodecanoyloxy)propan-2-yl)oxy)-4-oxobutanoic acid (6A): To a solution of 2-hydroxypropane-1,3-diyl didodecanoate 4A (40.0 g, 0.087 mol) in chloroform (200 mL), dihydrofuran-2,5-dione 5 (10.50 g, 0.105 mol) and triethylamine (18.50 mL, 0.131 mol) were added at room temperature. The reaction mixture was stirred at 120° C. for 3 h. After completion, reaction mixture was diluted with water (200 mL) and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 25 to 30% ethyl acetate in hexanes to afford the desired product 6A as white solid. Yield: 20.0 g, 41%.

MS (ESI) m/z 555.40[M−1];

$^1$H NMR (400 MHz, DMSO-d6); δ 12.30 (s, 1H), 5.17 (m, 1H), 4.18-4.25 (m, 4H), 2.50-2.47 (m, 8H), 1.23-1.25 (m, 36H), 0.83 (m, 6H).

Synthesis of 4-((1,3-bis(dodecanoyloxy)propan-2-yl)oxy)-4-oxobutanoate1-(2-((2,4-dichlorobenzyl)oxy)-2-(2,4-dichlorophenyl)ethyl)-1H-imidazol-1-ium (8)
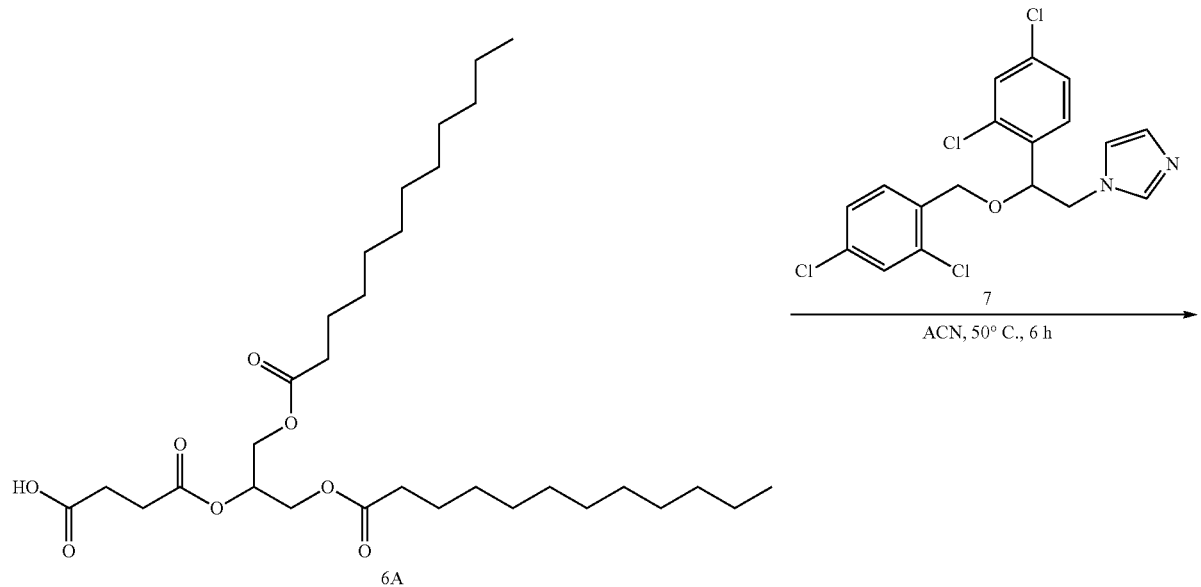
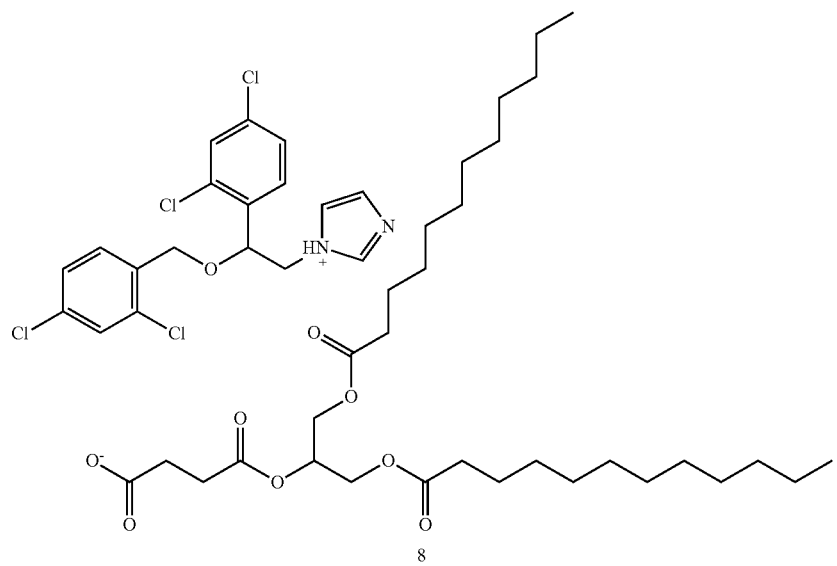

To a solution of 4-((1,3-bis(dodecanoyloxy)propan-2-yl)oxy)-4-oxobutanoic acid 6A (6.0 g, 0.013 mol) in acetonitrile (150 mL) was added 1-(2-((2,4-dichlorobenzyl)oxy)-2-(2,4-dichlorophenyl)ethyl)-1H-imidazole 7 (5.62 g, 0.013 mol) at ambient temperature. The resulting reaction mixture was heated up to 50° C. for next 6 h followed by the evaporation of solvent under reduced pressure to get the desired product 8 as colorless viscous oil. Yield: 11.62 g, quant.

Synthesis of 4-((1,3-bis(dodecanoyloxy)propan-2-yl)oxy)-4-oxobutanoate 1-((2-chlorophenyl)diphenylmethyl)-1H-imidazol-3-ium 10

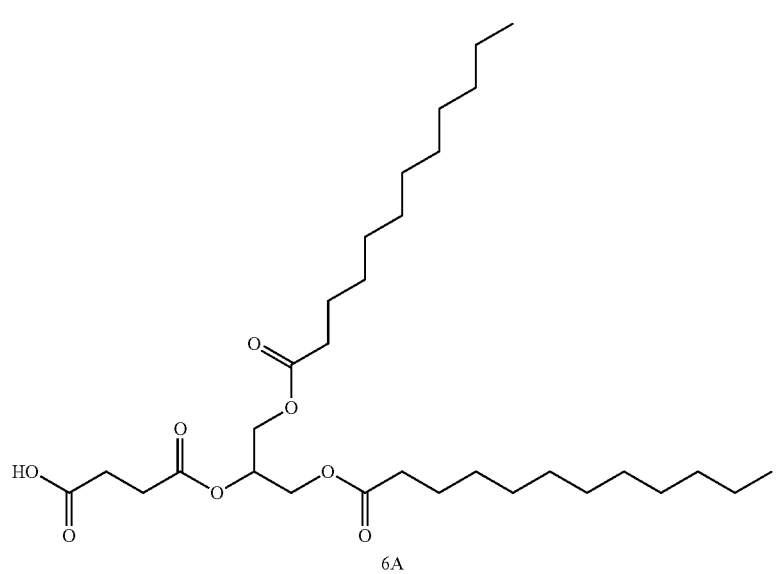

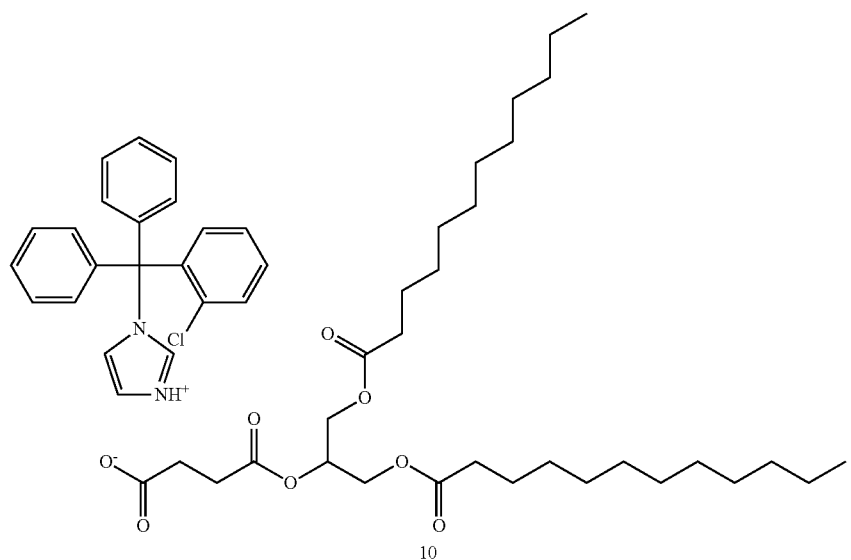

To a solution of 4-((1,3-bis(dodecanoyloxy)propan-2-yl)oxy)-4-oxobutanoic acid 6A (7.0 g, 0.016 mol) in acetonitrile (150 mL) was added 1-((2-chlorophenyl)diphenylmethyl)-1H-imidazole 9 (5.52 g, 0.016 mol) at ambient temperature. The resulting reaction mixture was heated up to 50° C. for next 6 h followed by the evaporation of solvent under reduced pressure to get the desired product 10 as white semi solid. Yield: 12.52 g, quant.

Synthesis of 4-((1,3-bis(dodecanoyloxy)propan-2-yl)oxy)-4-oxobutanoate 1-((4-((4-(4-(4-(1-(sec-butyl)-5-oxo-1,5-dihydro-4H-1,2,4-triazol-4-yl)phenyl)piperazin-1-yl) phenoxy)methyl)-2-(2,4-dichlorophenyl)-1,3-dioxolan-2-yl)methyl)-1H-1,2,4-triazol-1-ium 12

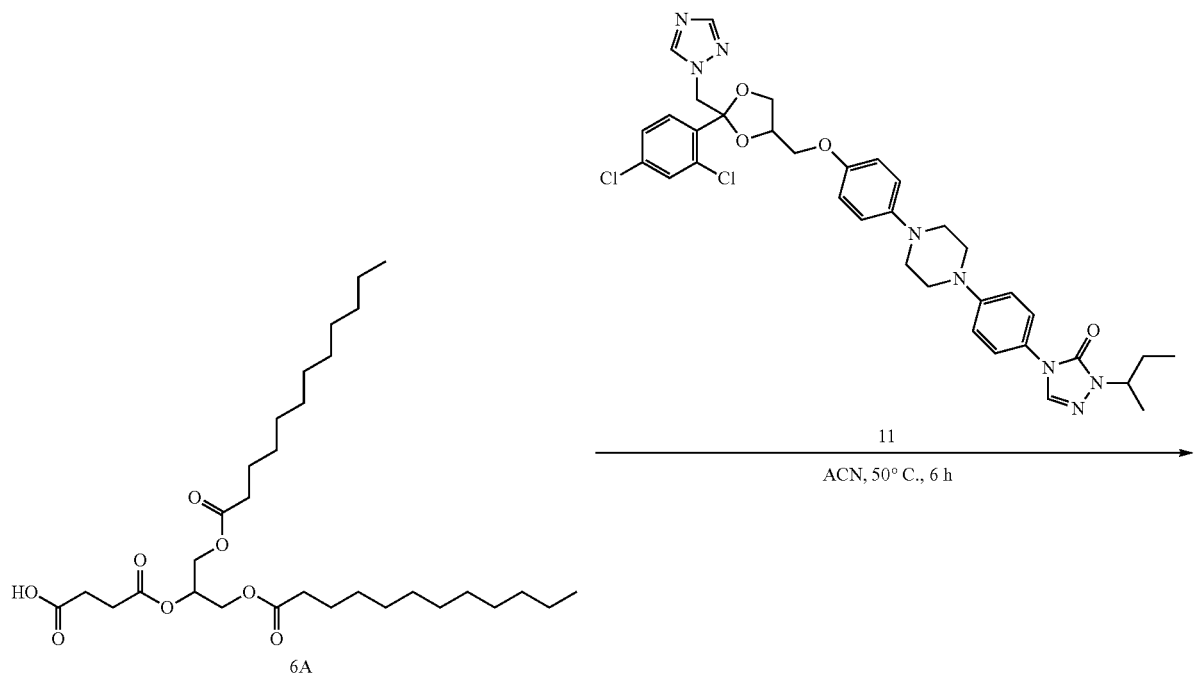

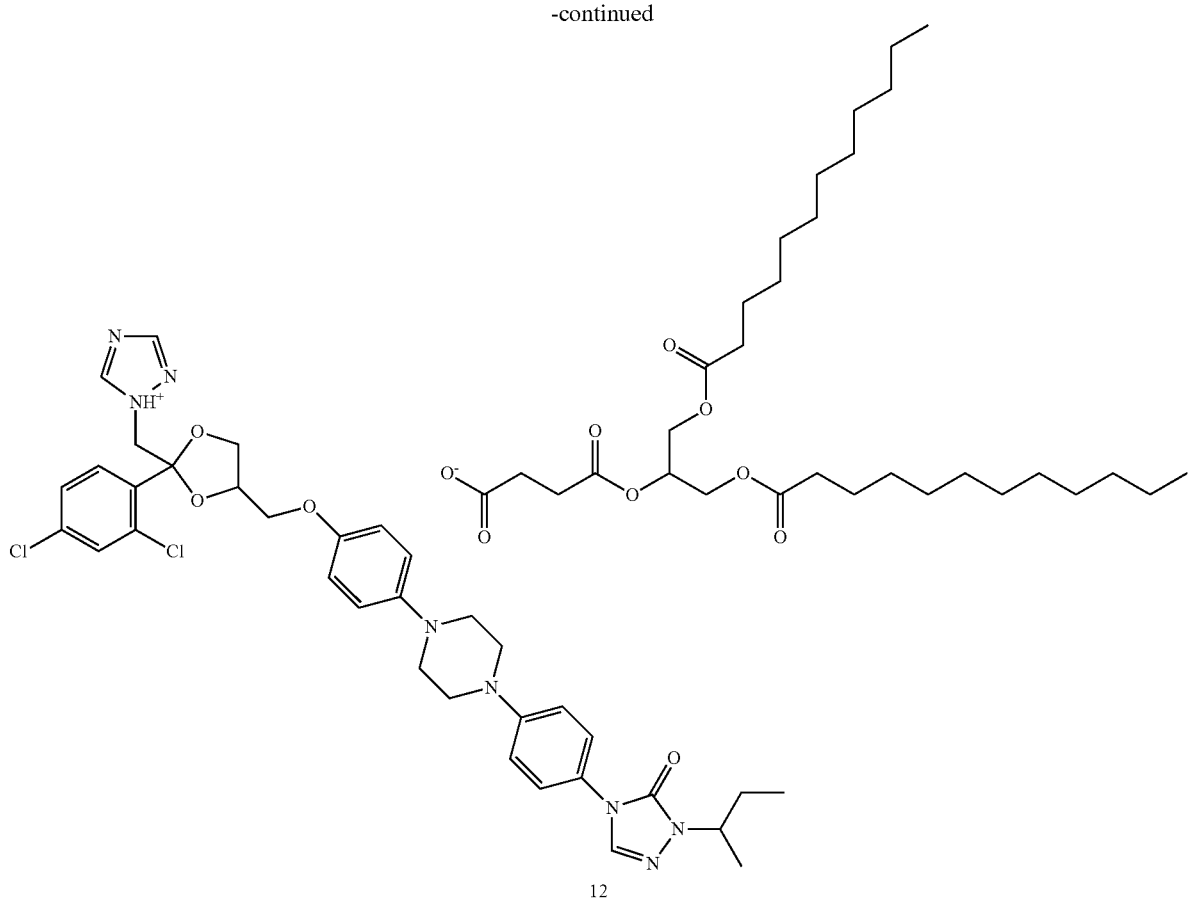

To a solution of 4-((1,3-bis(dodecanoyloxy)propan-2-yl)oxy)-4-oxobutanoic acid 6A (6.0 g, 0.013 mol) in acetonitrile (150 mL) was added 4-(4-(4-(4-((2-((1H-1,2,4-triazol-1-yl)methyl)-2-(2,4-dichlorophenyl)-1,3-dioxolan-4-yl)methoxy)phenyl)piperazin-1-yl)phenyl)-2-(sec-butyl)-2,4-dihydro-3H-1,2,4-triazol-3-one 11 (9.17 g, 0.013 mol) at ambient temperature. The resulting reaction mixture was heated up to 50° C. for next 6 h followed by the evaporation of solvent under reduced pressure to get the desired product 12 as off-white solid. Yield: 15.17 g, quantitative.

Synthesis of 4-((1,3-bis(octanoyloxy)propan-2-yl)oxy)-4-oxobutanoate 4-(4-(((3R,5R)-5-((1H-1,2,4-triazol-1-yl)methyl)-5-(2,4-difluorophenyl)tetrahydrofuran-3-yl)methoxy) phenyl)-1-(4-(1-((2S,3S)-2-hydroxypentan-3-yl)-5-oxo-1,5-dihydro-4H-1,2,4-triazol-4-yl)phenyl)piperazin-1-ium 14 [Formula I]
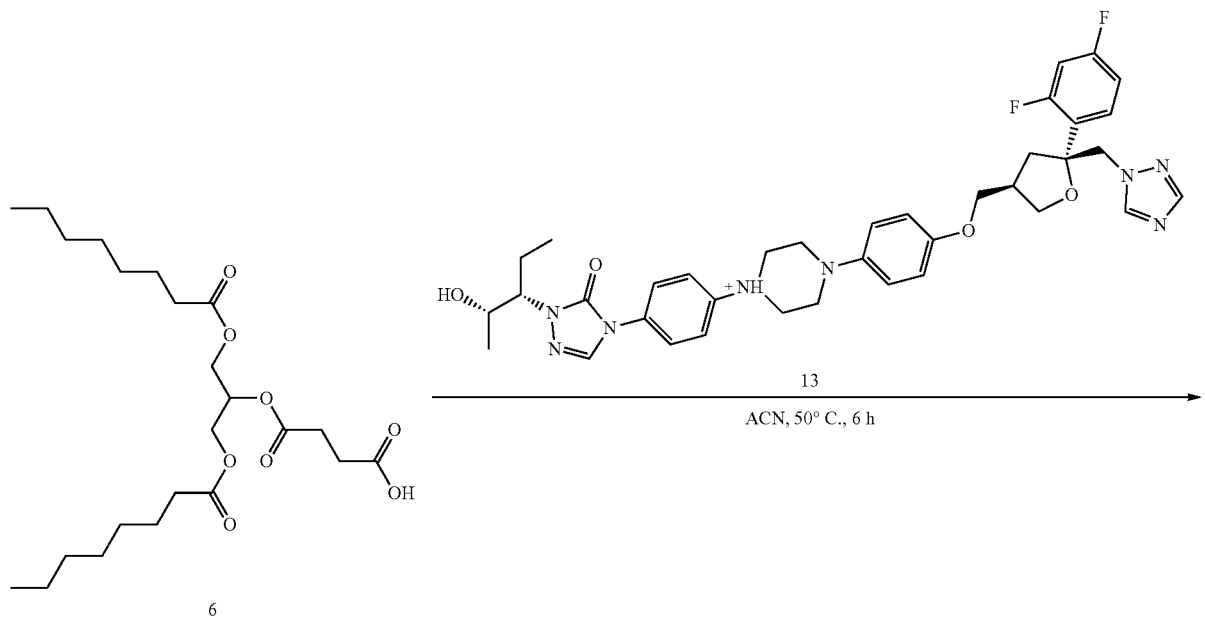

To a solution of 4-((1,3-bis(octanoyloxy)propan-2-yl)oxy)-4-oxobutanoic acid 6 (4.20 g, 0.009 mol) in acetonitrile (100 mL) was added 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-2-((2S,3S)-2-hydroxypentan-3-yl)-2,4-dihydro-3H-1,2,4-triazol-3-one 13 (6.63 g, 0.009 mol) at ambient temperature. The resulting reaction mixture was heated up to 50° C. for next 6 h followed by the evaporation of solvent under reduced pressure to get the desired product 14, FORMULA I as off-white hygroscopic solid. Yield: 10.83 g, quant.

Synthesis of 4-((1,3-bis(octanoyloxy)propan-2-yl)oxy)-4-oxobutanoate 4-((2S,3R)-3-(2,4-difluorophenyl)-3-hydroxy-4-(1H-1,2,4-triazol-1-yl)butan-2-yl)-5-fluoropyrimidin-1-ium 16 [FORMULA II]

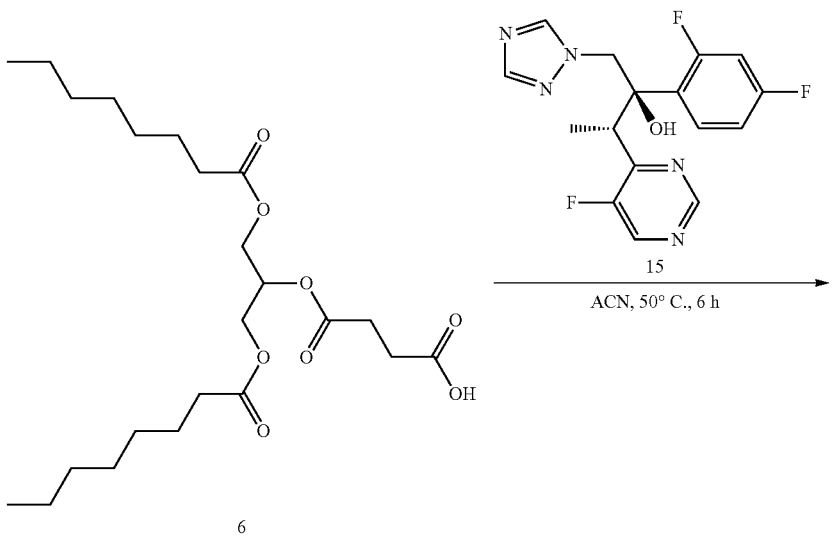

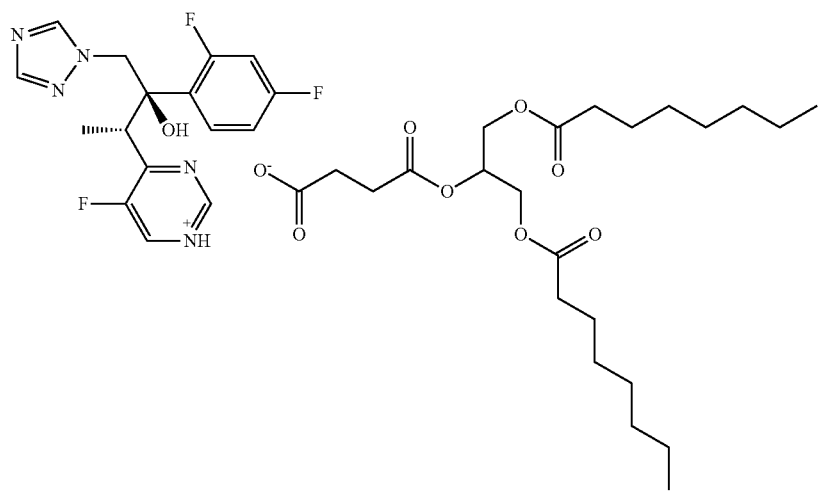

To a solution of 4-((1,3-bis(octanoyloxy)propan-2-yl)oxy)-4-oxobutanoic acid 6 (6.0 g, 0.013 mol) in acetonitrile (150 mL) was added (2R,3S)-2-(2,4-difluorophenyl)-3-(5-fluoropyrimidin-4-yl)-1-(1H-1,2,4-triazol-1-yl)butan-2-ol 15 (4.72 g, 0.013 mol) at ambient temperature. The resulting reaction mixture was heated up to 50° C. for next 6 h followed by the evaporation of solvent under reduced pressure to get the desired product 16, FORMULA II as off-white semi solid. Yield: 10.72 g, quantitative.

Synthesis of 4-((1,3-bis(octanoyloxy)propan-2-yl)oxy)-4-oxobutanoate N,6,6-trimethyl-N-(naphthalen-1-ylmethyl)hept-2-en-4-yn-1-aminium 18

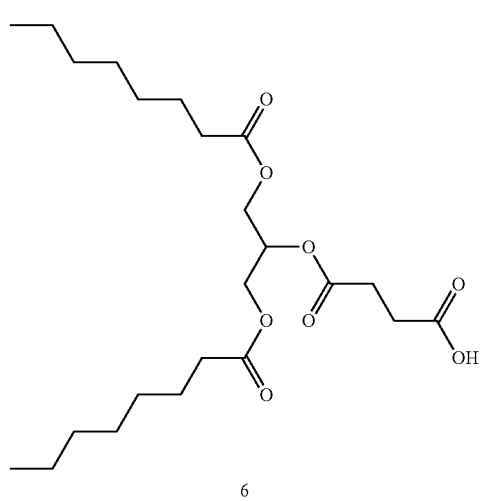

6

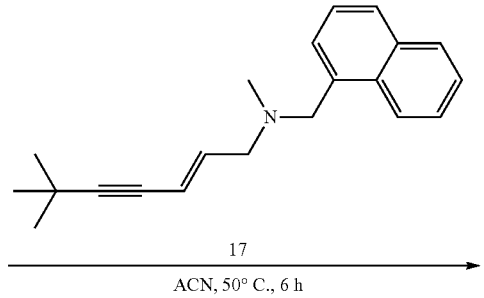

17
ACN, 50° C., 6 h

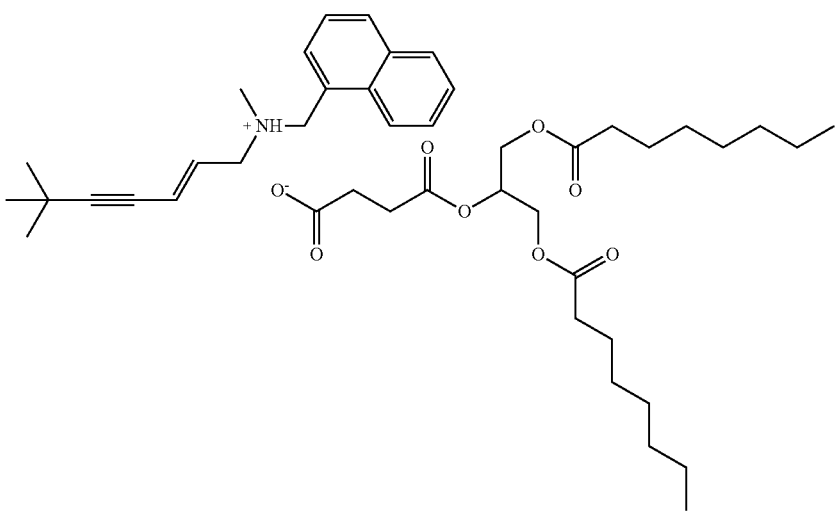

18

To a solution of 4-((1,3-bis(octanoyloxy)propan-2-yl)oxy)-4-oxobutanoic acid 6 (6.50 g, 0.014 mol) in acetonitrile (150 mL) was added N,6,6-trimethyl-N-(naphthalen-1-ylmethyl)hept-2-en-4-yn-1-amine 17 (4.20 g, 0.014 mol) at ambient temperature. The resulting reaction mixture was heated up to 50° C. for next 6 h followed by the evaporation of solvent under reduced pressure to get the desired product 18, FORMULA III as colorless liquid. Yield: 10.70 g, quantitative.

Synthesis of 4-((1,3-bis(octanoyloxy)propan-2-yl)oxy)-4-oxobutanoate N-(4-(tert-butyl)benzyl)-N-methyl-1-(naphthalen-1-yl)methanaminium 20

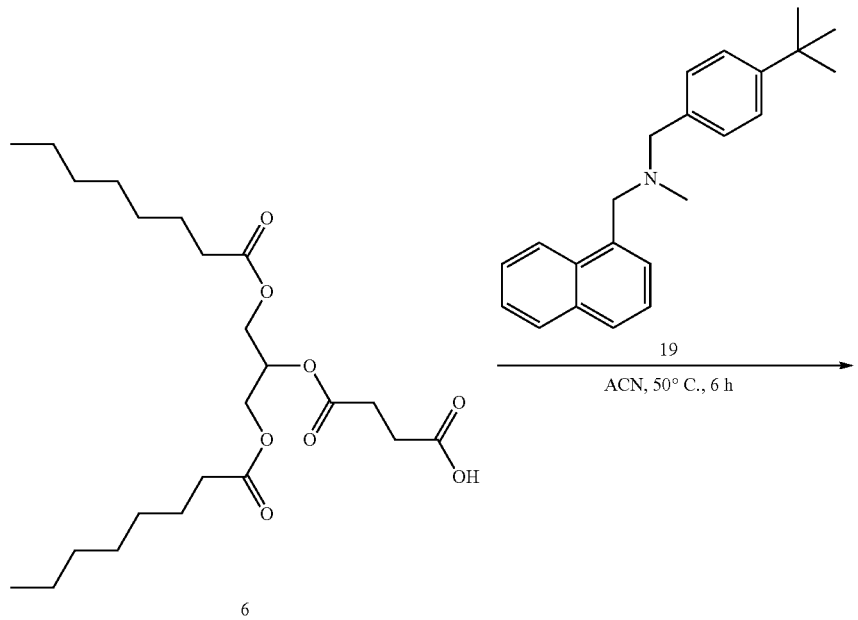

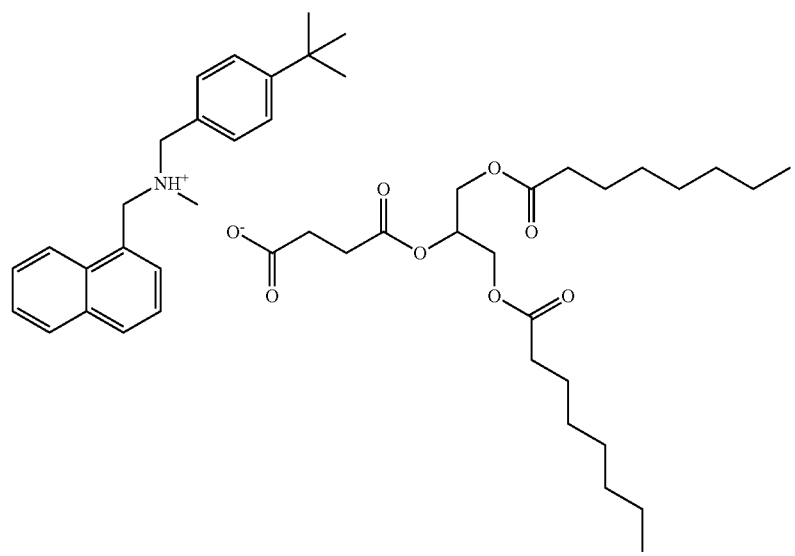

To a solution of 4-((1,3-bis(octanoyloxy)propan-2-yl)oxy)-4-oxobutanoic acid 6 (6.0 g, 0.013 mol) in acetonitrile (150 mL) was added N-(4-(tert-butyl)benzyl)-N-methyl-1-(naphthalen-1-yl)methanamine 19 (4.29 g, 0.013 mol) at ambient temperature. The resulting reaction mixture was heated up to 50° C. for next 6 h followed by the evaporation of solvent under reduced pressure to get the desired product 20, FORMULA IV as colorless liquid. Yield: 10.29 g, quantitative.

Synthesis of 4-((1,3-bis(octanoyloxy)propan-2-yl)oxy)-4-oxobutanoate 5-fluoro-2-oxo-2,3-dihydropyrimidin-4-aminium 22

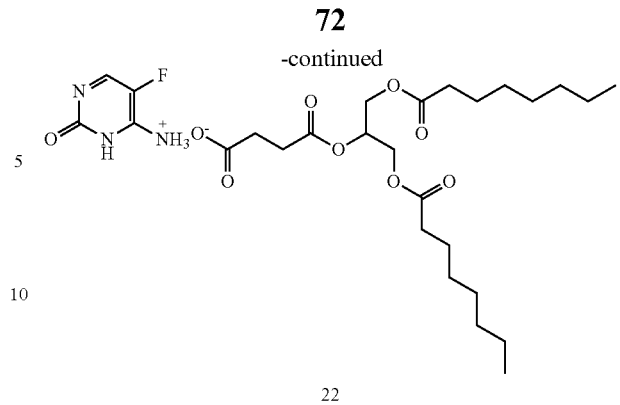

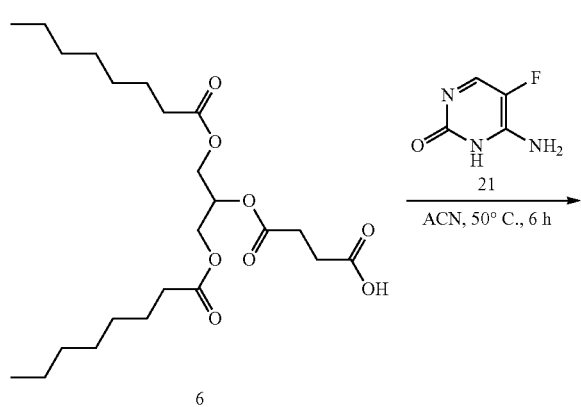

To a solution of 4-((1,3-bis(octanoyloxy)propan-2-yl)oxy)-4-oxobutanoic acid 6 (8.0 g, 0.018 mol) in acetonitrile (150 mL) was 6-amino-5-fluoropyrimidin-2(1H)-one 17 (2.52 g, 0.018 mol) at ambient temperature. The resulting reaction mixture was heated up to 50° C. for next 6 h followed by the evaporation of solvent under reduced pressure to get the desired product 22, FORMULA V as off-white semi solid (hygroscopic). Yield: 10.52 g, quantitative.

Synthesis of (E)-4-((1,3-bis(dodecanoyloxy)propan-2-yl)oxy)-4-oxobut-2-enoic acid

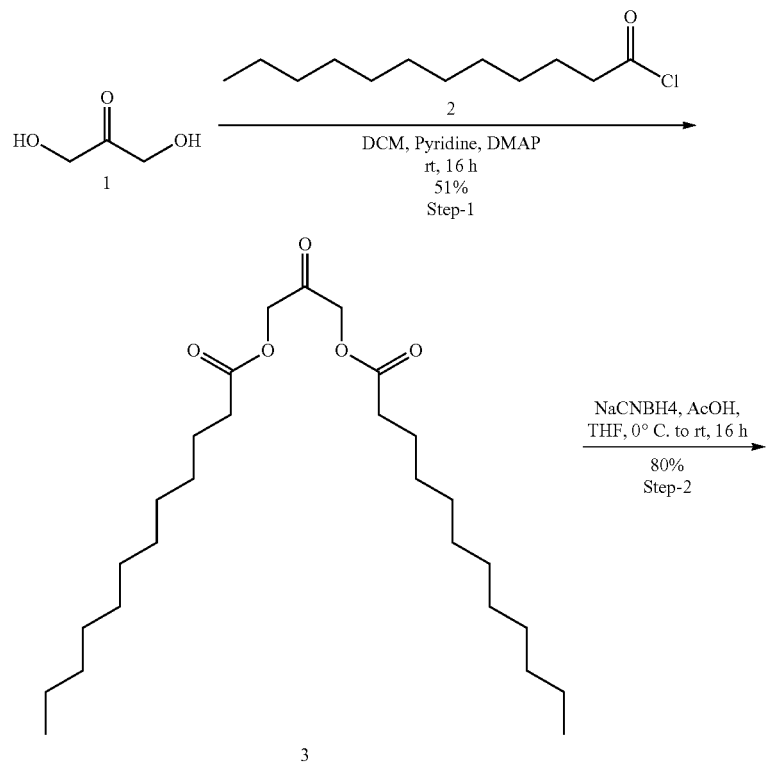

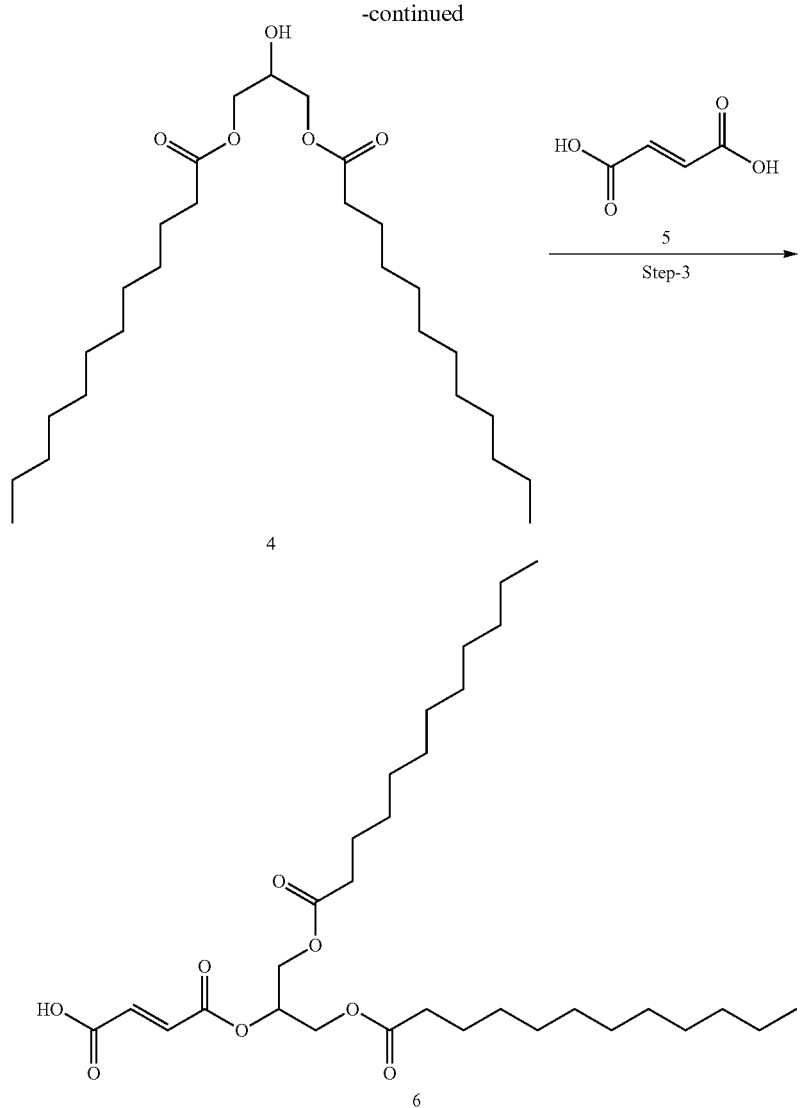

Synthesis of 2-oxopropane-1,3-diyl didodecanoate (3): To an ice cold solution of 1,3-dihydroxypropan-2-one (1, 30.0 g, 0.33 mol) in dichloromethane (500 mL) was added 4-dimethylaminopyridine (20.30 g, 0.167 mol) and pyridine (107 mL, 0.1.332 mol) and stirred for next 5 min. To the above reaction mixture dodecanoyl chloride 2 (218.50 g, 1.167 mol) was added dropwise at 0° C. and the reaction mixture was stirred at room temperature for 16 h. After completion, reaction mixture was filtered, the solid was washed with dichloromethane (100 mL), filtrate was washed with brine (200 mL), saturated solution of sodium bicarbonate (200 mL) and 0.1 N HCl solution (100 mL). The organic layer was separated, dried over anhydrous sodium sulfate and solvent was removed under reduced pressure to get crude. The crude was triturated with diethyl ether to afford the desired product 3 as white solid. Yield: 78 g, 51%. MS (ESI) m/z 455.37[M+1]+; 1H NMR (400 MHz, DMSO-d6): δ 4.74 (s, 4H), 2.43 (m, 4H), 1.64 (m, 4H), 1.55-1.25 (m, 32H), 0.87 (m, 6H).

Step-2: Synthesis of 2-hydroxypropane-1,3-diyl didodecanoate (4): To an ice cold solution of 2-oxopropane-1,3-diyl didodecanoate 3 (75.0 g, 0.165 mol) in THF (1000 mL) was added drop wise acetic acid (15 mL) followed by the portion wise addition of sodium cyanoborohydride (12.41 g, 0.198 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude was triturated with diethyl ether to afford the desired product 4 as white solid. Yield: 60.0 g, 80%. MS (ESI) m/z 457.48[M+1]+; 1H NMR (400 MHz, DMSO-d6): δ 5.26 (d, J=5.2 Hz, 1H), 3.92-3.98 (m, 4H), 2.28 (m, 4H), 1.50 (m, 4H), 1.23 (m, 33H) and 0.83 (m, 6H).

Step-3: Synthesis of (E)-4-((1,3-bis(dodecanoyloxy)propan-2-yl)oxy)-4-oxobut-2-enoic acid (6): To an ice-cold solution of 2-hydroxypropane-1,3-diyl didodecanoate 4 (10.0 g, 21.91 mmol) in THF (170 mL) was added fumaric acid 5 (2.54 g, 21.91 mmol), benzoyl chloride (2.5 mL, 21.91 mmol) and DMAP (0.67 g, 5.477 mmol). The resulting mixture was stirred at RT for 16 h. After completion of reaction (TLC monitoring), reaction mixture was concentrated under reduced pressure. The crude was diluted with water (200 mL), adjust pH ~2-3 using 1N—HCl and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 80% ethyl acetate in hexanes to afford the desired product 6 as white solid. Yield: 400 mg, 3.30% (un-optimized yield). LC-MS: m/z 553.64 [M−1]; 97.27% purity. 1H NMR (400 MHz, DMSO-d6): δ 13.26 (br s, 1H), 5.17 (d, J=15.8 Hz, 2H), 5.29 (m, 1H), 4.30-4.33 (m, 2H), 4.19-4.23 (m, 2H), 2.28 (m, 4H), 1.48 (m, 4H), 1.22 (m, 32H) and 0.83 (m, 6H).

Synthesis of (E)-4-((1,3-bis(dodecanoyloxy)propan-2-yl)oxy)-4-oxobut-2-enoate 1-((4-((4-(4-(4-(1-(sec-butyl)-5-oxo-1,5-dihydro-4H-1,2,4-triazol-4-yl)phenyl)piperazin-1-yl)phenoxy)methyl)-2-(2,4-dichlorophenyl)-1,3-dioxolan-2-yl)methyl)-1H-1,2,4-triazol-1-ium (8)

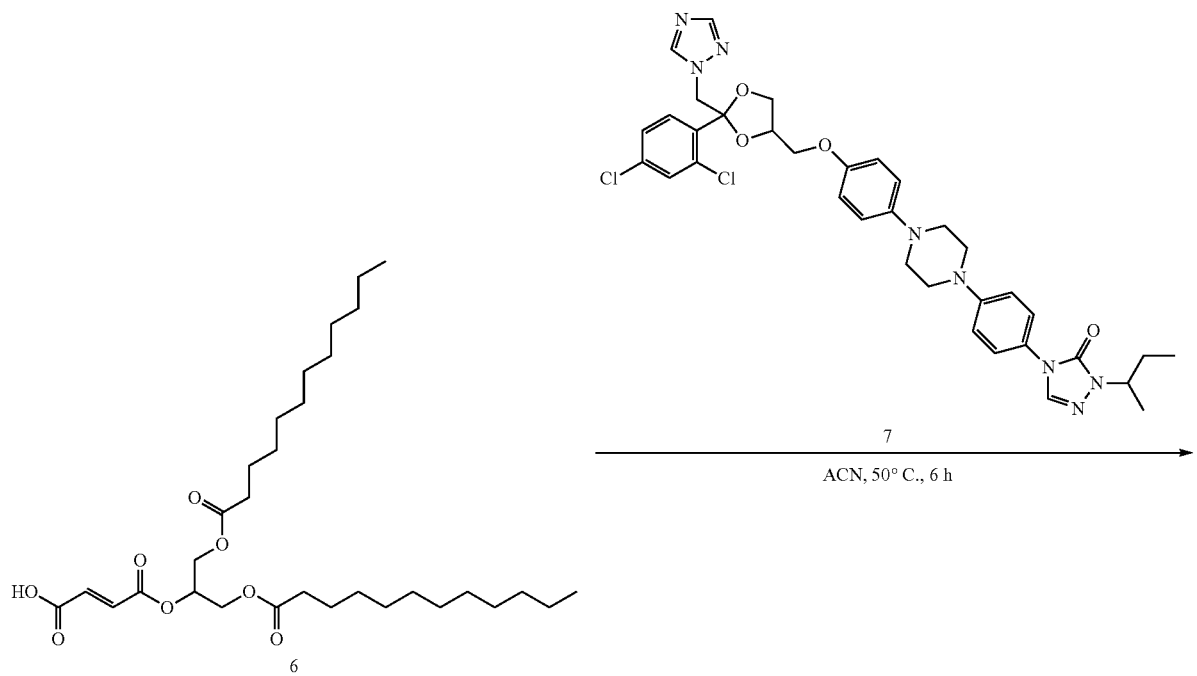

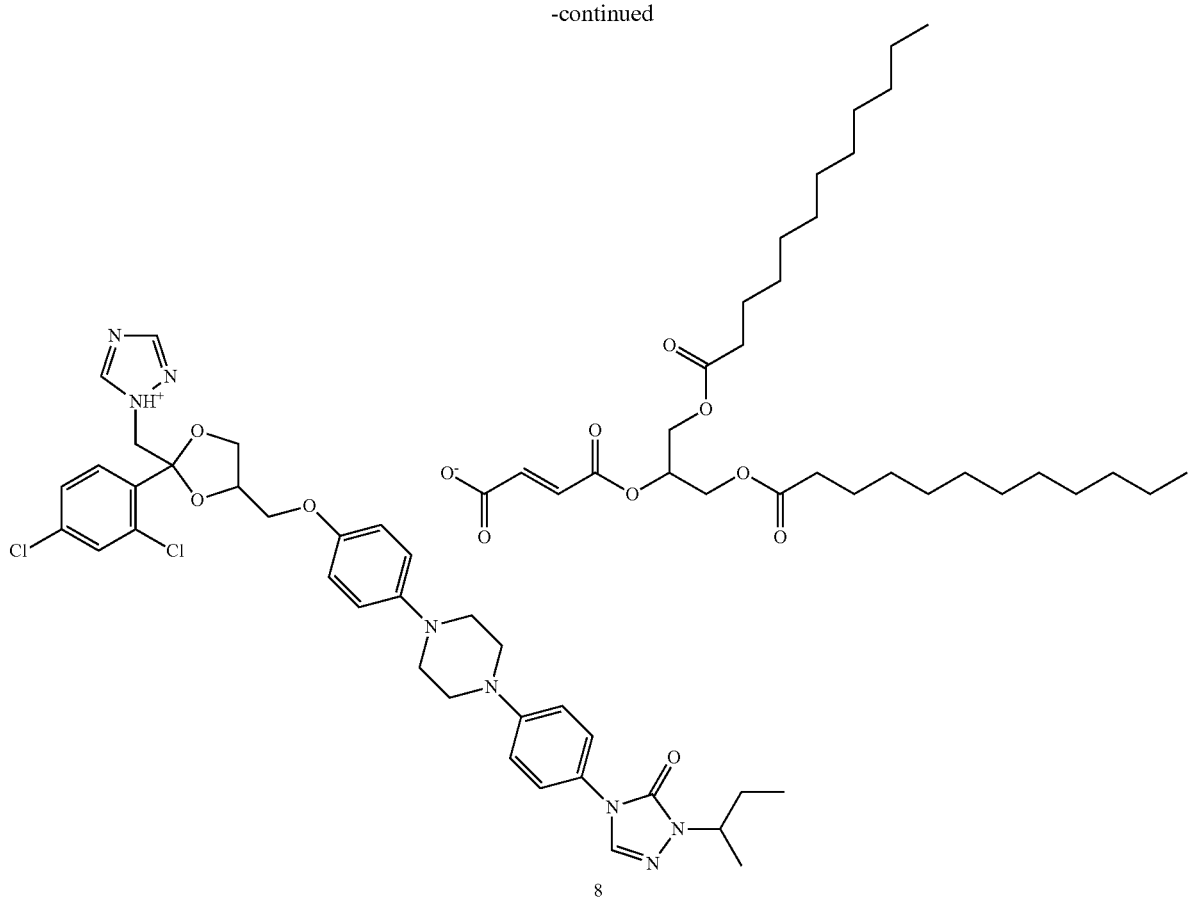

8

To a solution of (E)-4-((1,3-bis(dodecanoyloxy)propan-2-yl)oxy)-4-oxobut-2-enoic acid 6 (100 mg, 0.18 mmol) in acetonitrile (5 mL) was added 4-(4-(4-(4-((2-((1H-1,2,4-triazol-1-yl)methyl)-2-(2,4-dichlorophenyl)-1,3-dioxolan-4-yl)methoxy)phenyl) piperazin-1-yl)phenyl)-2-(sec-butyl)-2,4-dihydro-3H-1,2,4-triazol-3-one 7 (127 mg, 0.18 mmol) at ambient temperature. The resulting reaction mixture was heated up to 50° C. for next 3 h followed by the evaporation of solvent under reduced pressure to get the desired product 8 as white solid (M.P. 73.9° C.); yield: 225 mg, quantitative.

Synthesis of (E)-4-((1,3-bis(dodecanoyloxy)propan-2-yl)oxy)-4-oxobut-2-enoate 4-(4-(((3R,5R)-5-((1H-1,2,4-triazol-1-yl)methyl)-5-(2,4-difluorophenyl) tetrahydrofuran-3-yl) methoxy)phenyl)-1-(4-(1-((2S, 3S)-2-hydroxypentan-3-yl)-5-oxo-1,5-dihydro-4H-1, 2,4-triazol-4-yl)phenyl)piperazin-1-ium (10)

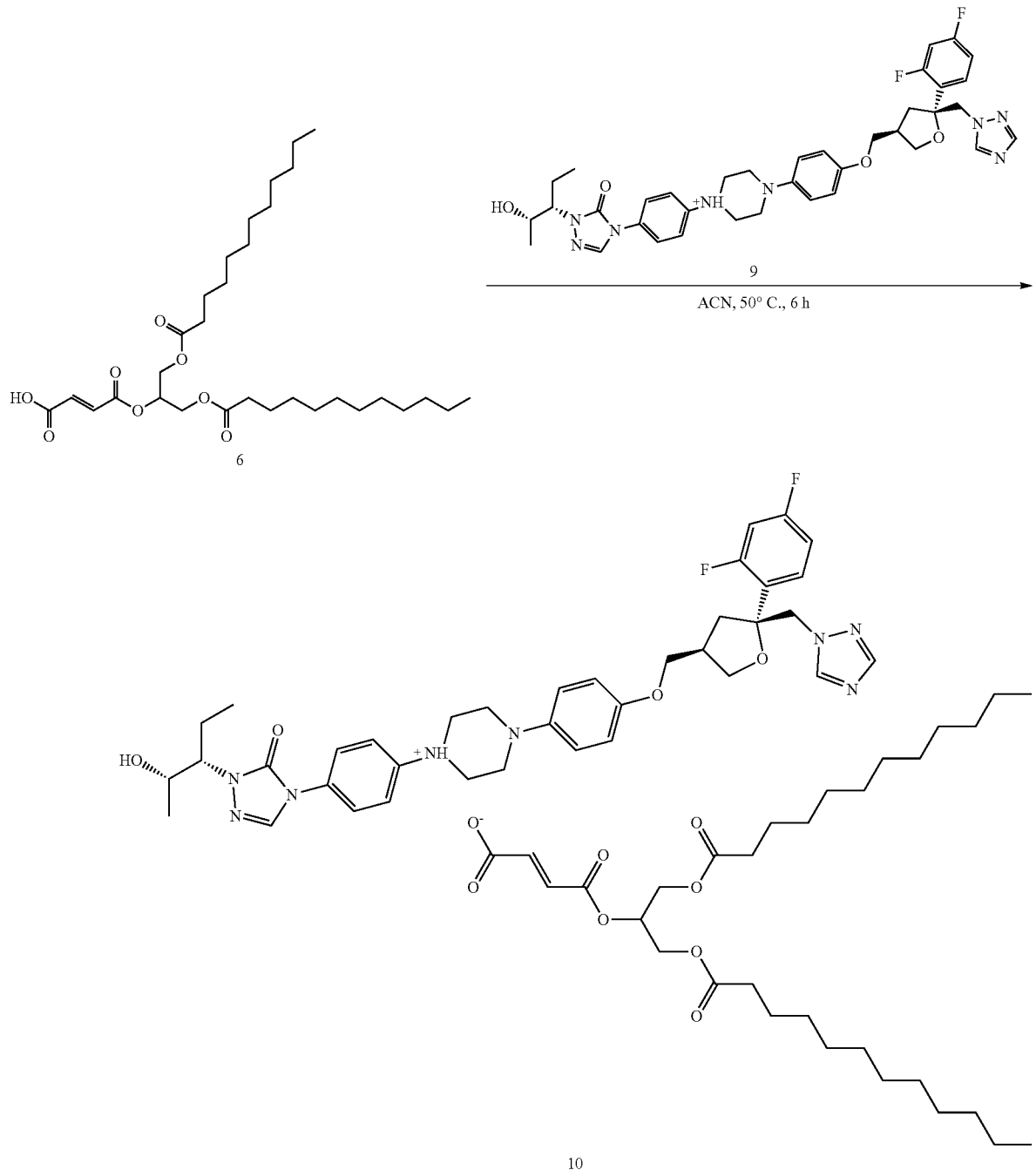

To a solution of (E)-4-((1,3-bis(dodecanoyloxy)propan-2-yl)oxy)-4-oxobut-2-enoic acid 6 (100 mg, 0.18 mmol) in acetonitrile (5 mL) was added 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-2-((2S,3S)-2-hydroxypentan-3-yl)-2,4-dihydro-3H-1,2,4-triazol-3-one 9 (126 mg, 0.18 mmol) at ambient temperature. The resulting reaction mixture was heated up to 50° C. for next 3 h followed by the evaporation of solvent under reduced pressure to get the desired product 10 as off-white solid (M.P. 78.6° C.), yield: 225 mg, quant.

Synthesis of (E)-4-((1,3-bis(dodecanoyloxy)propan-2-yl)oxy)-4-oxobut-2-enoate 4-((2S,3R)-3-(2,4-difluorophenyl)-3-hydroxy-4-(1H-1,2,4-triazol-1-yl)butan-2-yl)-5-fluoropyrimidin-1-ium (12)

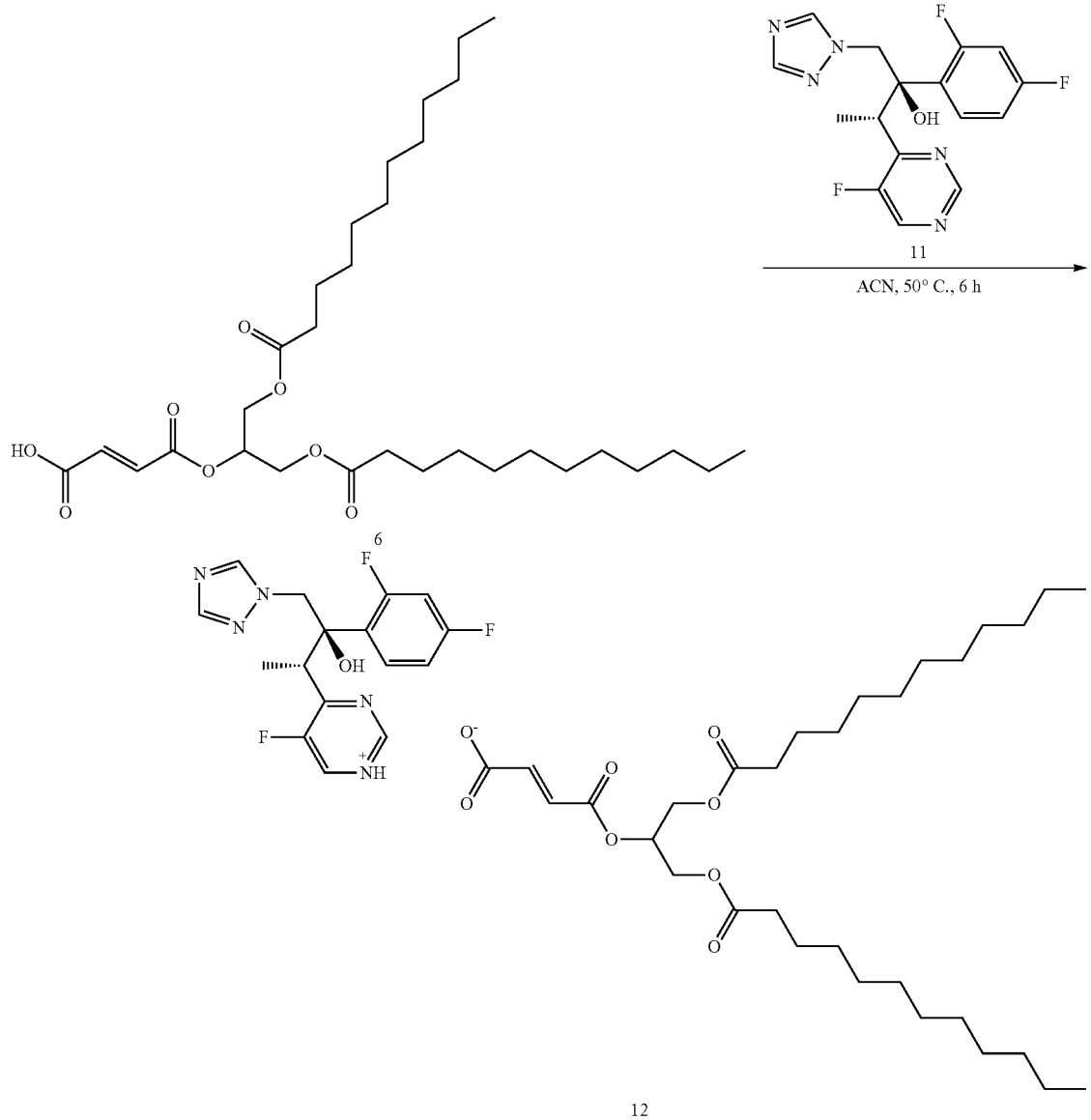

To a solution of (E)-4-((1,3-bis(dodecanoyloxy)propan-2-yl)oxy)-4-oxobut-2-enoic acid 6 (100 mg, 0.18 mmol) in acetonitrile (5 mL) was added 1-(2-((2,4-dichlorobenzyl)oxy)-2-(2,4-dichlorophenyl)ethyl)-1H-imidazole 11 (63 mg, 0.18 mmol) at ambient temperature. The resulting reaction mixture was heated up to 50° C. for next 3 h followed by the evaporation of solvent under reduced pressure to get the desired product 12 as off-white solid (M.P. 71.4° C.), yield: 130 mg, quant.

Anti-Microbial Properties of Fatty Acids:

The antibacterial mode of action of Free Fatty Acids (FFA) is still poorly understood, the prime target of FFA action is the cell membrane, where FFAs disrupt the electron transport chain and oxidative phosphorylation; also it can interfere with cellular energy production, generation of peroxidation and auto-oxidation degradation products or direct lysis of bacterial cells. Medium-chain saturated fatty acids that lack a kinked structure can be packed more tightly and can reduce membrane fluidity and disrupt electron transport perhaps by restricting the movement of carriers within the membrane. The antibacterial effect of long chain unsaturated fatty acids were due to their inhibition of fatty acid biosynthesis.

Linoleic acid is GRAS listed long chain fatty acid. Among the long-chain fatty acids, arachidonic acid, linoleic acid, γ-linoleic acid, palmitoleic acid, and palmitic acid had the greatest antimicrobial activity. Linoleic acid was bactericidal at a concentration of 25 µg/ml; the mean % inhibition was between 80 to 100% for *S. mutans; A. actinomycetemcomitans; P. gingivalis; S. gordonii; S. sanguis*. Its activity against *C. albicans* was <40%, MIC for linoleic acid against the *Candida* Species was 0.45 µmoles/ml (which corresponds to 130 ng/ml). The minimum inhibitory concentration for linoleic acid against *Porphyromonas gingivalis* was 9 to 78 mcg/ml.

In vitro studies have suggested that gamma linoleic acid (GLA) has significant anti-microbial activity against the various oral pathogenic microorganisms.

The n-6 fatty acids GLA were bactericidal at a concentration of 25 µg/mL. These fatty acid and their esters also showed antimicrobial activity against the periodontopathogens, *A. actinomycetemcomitans*, and *P. gingivalis*, although they were generally most active against the oral streptococci. GLA and their methyl and ethyl esters were found to have antimicrobial activities against various oral microorganisms, including *S. mutans, A. actinomycetemcomitans, C. albicans, P. gingivalis, F. nucleatum*, and *S. gordonii*.

EQUIVALENTS

The present disclosure provides among other things compositions and methods for treating neurological diseases and their complications. While specific embodiments of the subject disclosure have been discussed, the above specification is illustrative and not restrictive. Many variations of the systems and methods herein will become apparent to those skilled in the art upon review of this specification. The full scope of the claimed systems and methods should be determined by reference to the claims, along with their full scope of equivalents, and the specification, along with such variations.

INCORPORATION BY REFERENCE

All publications and patents mentioned herein, including those items listed above, are hereby incorporated by reference in their entirety as if each individual publication or patent was specifically and individually indicated to be incorporated by reference. In case of conflict, the present application, including any definitions herein, will control.

The invention claimed is:
1. A compound of formula IX

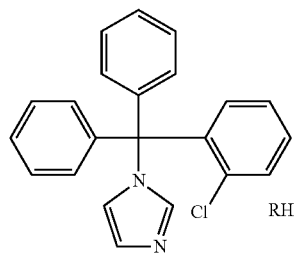

Formula IX or a pharmaceutically acceptable hydrate, solvate, enantiomer, or stereoisomer thereof,
wherein RH is selected from a group consisting of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid, caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hydrobromic acid, isobutyric acid, lactic acid, lactobionic acid, lauric acid, maleic acid, malic acid, malonic acid, mandelic acid, naphthalene-2-sulfonic acid, nicotinic acid, nitric acid, oleic acid, oxalic acid, palmitic acid, pamoic acid, proprionic acid, pyroglutamic acid, salicylic acid, sebacic acid, stearic acid, succinic acid, tartaric acid, thiocyanic acid, toluenesulfonic acid, undecylenic acid, omega 3 fatty acids, omega 6 fatty acids, n-acetyl cysteine, furoate, methyl furoate, ethyl furoate, aminocaproic acid, caprilic acid, alpha lipoic acid, R-lipoic acid, myristic acid, myristoleic acid, palmitic acid, palmitoleic acid, elaidic acid, linoleic acid, linolenic acid, linolelaidic acid and arachidonic acid or

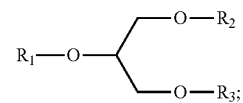

wherein
each $R_1$, $R_2$ and $R_3$ independently represents

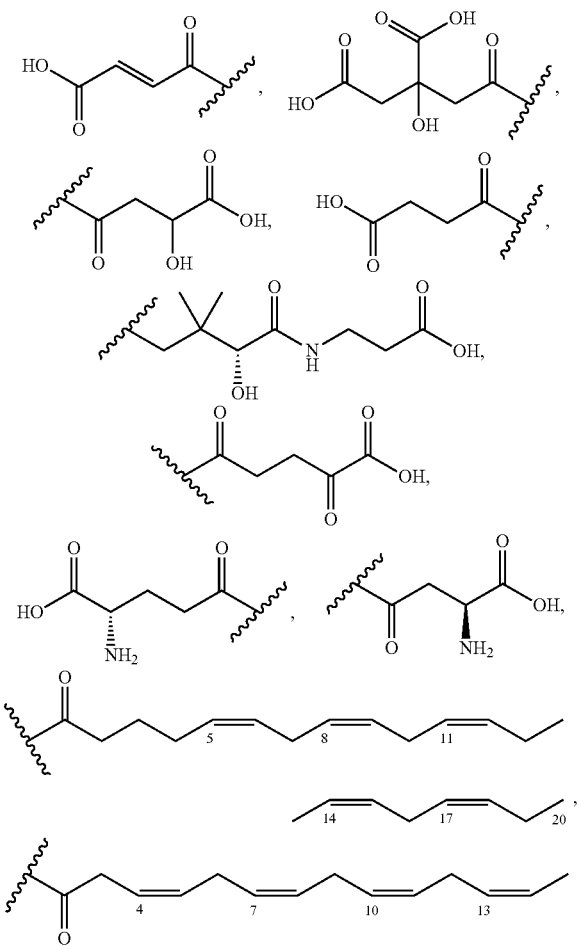

-continued

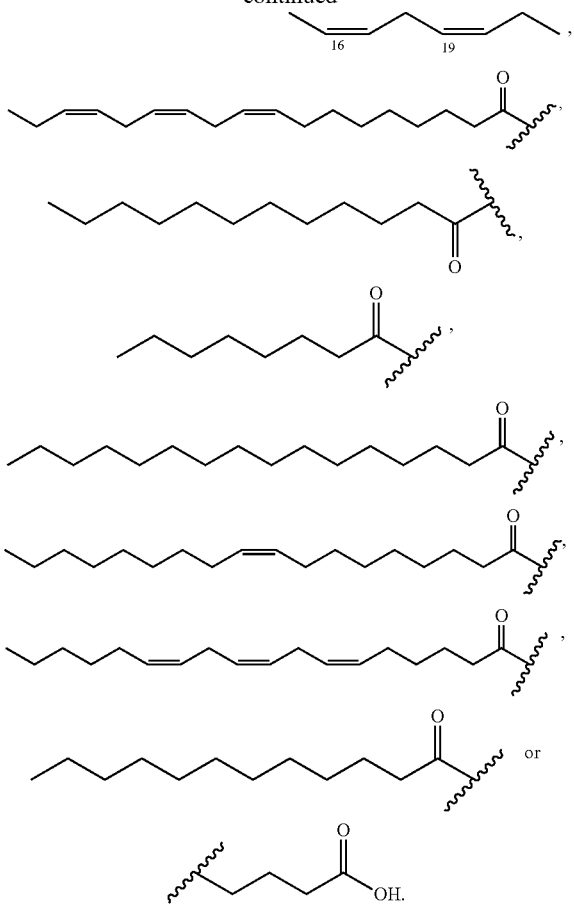

2. A pharmaceutical composition comprising a compound of claim 1 and a pharmaceutically acceptable carrier.

3. The pharmaceutical composition of claim 2, wherein said pharmaceutical composition is formulated with an effective amount of compound of claim 1 for oral administration, transmucosal administration, parenteral administration, intravenous administration, subdermal administration, rectal administration, buccal administration or transdermal administration.

4. The pharmaceutical composition of claim 3 wherein said pharmaceutical composition is formulated for the treatment of fungal infections, candidiasis or oral infectious diseases.

5. A compound of claim 1, wherein the compound has the chemical structure of:

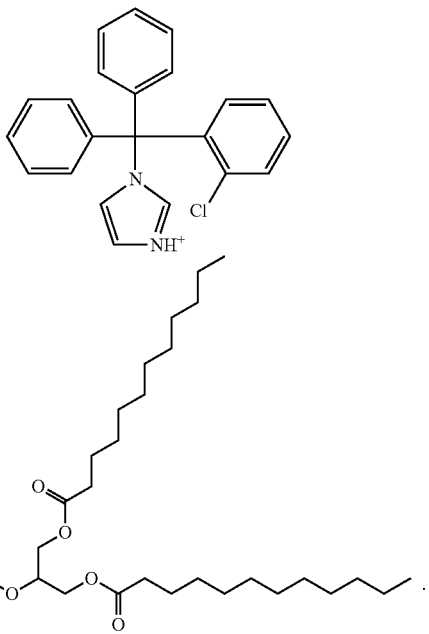

6. A pharmaceutical composition comprising a compound of claim 5 and a pharmaceutically acceptable carrier.

7. The pharmaceutical composition of claim 6, wherein said pharmaceutical composition is formulated with an effective amount of compound of claim 5 for oral administration, transmucosal administration, parenteral administration, intravenous administration, subdermal administration, rectal administration, buccal administration or transdermal administration.

8. The pharmaceutical composition of claim 7 wherein said pharmaceutical composition is formulated for the treatment of fungal infections, candidiasis or oral infectious diseases.

* * * * *